(12) United States Patent
Asirvatham et al.

(10) Patent No.: US 10,390,879 B2
(45) Date of Patent: Aug. 27, 2019

(54) DEVICES AND METHODS FOR ABLATION OF TISSUE

(71) Applicant: Mayo Foundation for Medical Education and Research, Rochester, MN (US)

(72) Inventors: Samuel J. Asirvatham, Rochester, MN (US); David R. Holmes, Jr., Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 818 days.

(21) Appl. No.: 14/892,035

(22) PCT Filed: May 20, 2014

(86) PCT No.: PCT/US2014/038722
§ 371 (c)(1),
(2) Date: Nov. 18, 2015

(87) PCT Pub. No.: WO2014/189887
PCT Pub. Date: Nov. 27, 2014

(65) Prior Publication Data
US 2016/0374754 A1    Dec. 29, 2016

Related U.S. Application Data

(60) Provisional application No. 61/902,384, filed on Nov. 11, 2013, provisional application No. 61/825,401, filed on May 20, 2013.

(51) Int. Cl.
*A61B 18/14* (2006.01)
*A61B 18/02* (2006.01)
(Continued)

(52) U.S. Cl.
CPC .......... *A61B 18/1492* (2013.01); *A61B 18/02* (2013.01); *A61B 2018/0022* (2013.01);
(Continued)

(58) Field of Classification Search
CPC ........ A61B 18/1492; A61B 2018/1465; A61B 2018/1467; A61B 2018/1472;
(Continued)

(56) References Cited

U.S. PATENT DOCUMENTS 5,868,736 A * 2/1999 Swanson ............ A61B 18/1492
606/34
6,012,457 A    1/2000 Lesh
(Continued)

FOREIGN PATENT DOCUMENTS

| WO | WO2008139232 A1 | 11/2008 |
| WO | WO2009036118 A1 | 3/2009 |
| WO | WO2012114333 A1 | 8/2012 |

OTHER PUBLICATIONS

Supplementary European Search Report in Application No. EP 14801752.8, dated Jun. 23, 2017, 17 pages.
(Continued)

*Primary Examiner* — Thomas A Giuliani
(74) *Attorney, Agent, or Firm* — Fish & Richardson P.C.

(57) ABSTRACT

This document provides devices and methods for the treatment of heart conditions, hypertension, and other medical disorders. For example, this document provides devices and methods for treating atrial fibrillation by performing thoracic vein ablation procedures, including pulmonary vein myocardium ablation. In some embodiments, the ablation is performed in coordination with the delivery a pharmacological agent that can abate the formation of tissue stenosis or neointimal hyperplasia caused by the ablation.

14 Claims, 11 Drawing Sheets

(51) Int. Cl.
  *A61B 18/00* (2006.01)
  *A61N 1/30* (2006.01)
  *A61B 90/00* (2016.01)
  *A61M 25/10* (2013.01)
(52) U.S. Cl.
  CPC .............. *A61B 2018/00065* (2013.01); *A61B 2018/00154* (2013.01); *A61B 2018/00351* (2013.01); *A61B 2018/00357* (2013.01); *A61B 2018/00375* (2013.01); *A61B 2018/00434* (2013.01); *A61B 2018/00577* (2013.01); *A61B 2090/3966* (2016.02); *A61M 2025/105* (2013.01); *A61N 1/306* (2013.01)
(58) Field of Classification Search
  CPC ........... A61B 2018/00154; A61B 2018/00351; A61B 2018/0016; A61B 2018/0022; A61B 2018/00238; A61B 2018/00375; A61B 2018/00357; A61B 2018/00065; A61B 2018/1266; A61B 2018/128; A61M 2025/105
  USPC ........ 606/41, 49; 607/98, 99, 101, 104, 105, 607/113, 115, 116, 119, 122
  See application file for complete search history.

(56) References Cited

U.S. PATENT DOCUMENTS

| | | | |
|---|---|---|---|
| 6,315,778 B1* | 11/2001 | Gambale | A61B 18/1492 606/41 |
| 6,491,710 B2 | 12/2002 | Satake | |
| 6,692,490 B1 | 2/2004 | Edwards | |
| 6,925,327 B2 | 8/2005 | Altman | |
| 7,192,438 B2 | 3/2007 | Margolis | |
| 8,043,351 B2 | 10/2011 | Yon et al. | |
| 8,347,891 B2 | 1/2013 | Demarais et al. | |
| 2002/0029062 A1 | 3/2002 | Satake | |
| 2002/0087156 A1* | 7/2002 | Maguire | A61B 18/00 606/41 |
| 2003/0144658 A1 | 7/2003 | Schwartz et al. | |
| 2003/0225338 A1 | 12/2003 | Altman | |
| 2004/0098030 A1 | 5/2004 | Makower | |
| 2004/0106952 A1 | 6/2004 | Lafontaine | |
| 2006/0224153 A1* | 10/2006 | Fischell | A61B 18/1492 606/41 |
| 2007/0149963 A1 | 6/2007 | Matsukuma et al. | |
| 2007/0225800 A1 | 9/2007 | Sahatjian | |
| 2007/0250050 A1 | 10/2007 | Lafontaine | |
| 2008/0086073 A1 | 4/2008 | McDaniel | |
| 2008/0249463 A1 | 10/2008 | Pappone | |
| 2008/0306570 A1 | 12/2008 | Rezai | |
| 2009/0228003 A1 | 9/2009 | Sinelnikov | |
| 2009/0247933 A1 | 10/2009 | Maor | |
| 2010/0125239 A1 | 5/2010 | Perry | |
| 2010/0249702 A1 | 9/2010 | Magana et al. | |
| 2010/0256629 A1* | 10/2010 | Wylie | A61B 18/1492 606/41 |
| 2010/0286684 A1 | 11/2010 | Hata | |
| 2011/0276047 A1* | 11/2011 | Sklar | A61B 18/1492 606/41 |
| 2012/0095395 A1 | 4/2012 | Haery | |
| 2013/0066312 A1 | 3/2013 | Subramaniam | |

OTHER PUBLICATIONS

Extended European Search Report in Eropean Application No. 14/801,752.80, dated Sep. 11, 2017, 15 pages.
International Search Report and Written Opinion for PCT/US2014/038722, dated Dec. 11, 2014, 17 pages.
International Preliminary Report on Patentability for PCT/US2014/038722, dated Dec. 3, 2015, 10 pages.
Gray and Granada, "Drug-coated balloons for the prevention of vascular restenosis," Circulation, 121(24):2672-80, Jun. 2010.
European Office Action dated Feb. 6, 2019 in European Application No. 14801752.8, 19 pages.

* cited by examiner

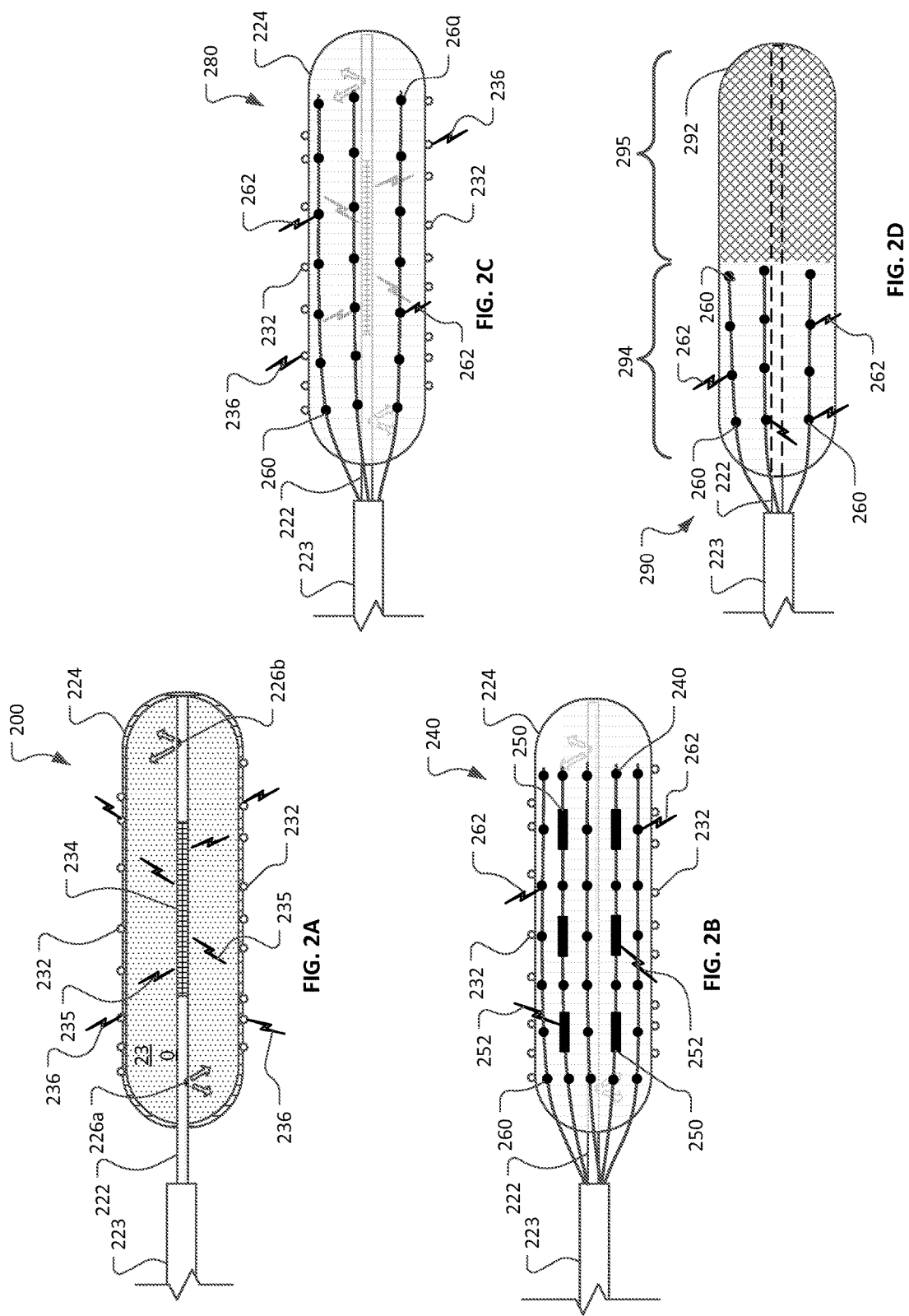

DEVICES AND METHODS FOR ABLATION OF TISSUE

CROSS-REFERENCE TO RELATED APPLICATIONS

This application is a National Stage application under 35 U.S.C. § 371 of International Application No. PCT/US2014/038722, having an International Filing Date of May 22, 2014, which claims the benefit of U.S. Provisional Application Ser. No. 61/902,384, filed Nov. 11, 2013, and U.S. Provisional Application Ser. No. 61/825,401, filed May 20, 2013. The disclosure of the prior applications are considered part of (and are incorporated by reference in) the disclosure of this application.

BACKGROUND

1. Technical Field

This document relates to devices and methods for the treatment of medical disorders including heart conditions and hypertension. For example, among other things this document relates to devices and methods for treating atrial fibrillation by performing thoracic vein ablation procedures, including pulmonary vein myocardium ablation. In some embodiments, the ablation procedures are performed in coordination with the delivery a pharmacological agent that can provide therapeutic effects such as the abatement of tissue stenosis or neointimal hyperplasia that may otherwise be caused by the ablation.

2. Background Information

Atrial fibrillation is an irregular and often rapid heart rate that commonly causes poor blood flow to the body. During atrial fibrillation, the heart's two upper chambers (the atria) beat chaotically and irregularly—out of coordination with the two lower chambers (the ventricles) of the heart. Atrial fibrillation symptoms include heart palpitations, shortness of breath, and weakness.

Ablation procedures, including ablation of thoracic veins such as the pulmonary vein, are a treatment for atrial fibrillation. During pulmonary vein ablation, catheters are inserted into the atrium. Energy is delivered from the catheter to the tissue of the pulmonary vein and/or near the ostia of the pulmonary veins in the left atrium. The energy delivered causes scarring of the tissue. The scars block impulses firing from within the pulmonary veins, thereby electrically "disconnecting" them or "isolating" them from the heart. This can provide restoration of normal heart rhythms.

However, an undesirable side effect of treatment of atrial fibrillation by pulmonary vein ablation is pulmonary vein stenosis and neointimal hyperplasia. Pulmonary vein stenosis is the narrowing of the vessels that carry blood from the lungs to the heart. Pulmonary vein stenosis can result in reduced cardiopulmonary efficiency and a decline in quality of life. In some cases, to reduce the effects of stenosis, only a partial circumference of the pulmonary vein is ablated. However, such partial-circumferential ablation procedures are generally less effective for eliminating atrial fibrillation in comparison to ablation of the entire circumference of the pulmonary veins and/or pulmonary vein ostia.

In some cases, ablation procedures can also be used advantageously in the renal arteries to treat hypertension. Ablation of the renal sympathetic nerves using catheter-delivered radiofrequency energy may be an effective intervention for uncontrolled hypertension in some instances. For example, such renal denervation procedures may be beneficial for at least some of the 20 to 30 percent of adults being treated for hypertension that do not achieve adequate blood pressure control with medications.

SUMMARY

This document provides devices and methods for treating atrial fibrillation, hypertension, and other medical disorders. Atrial fibrillation can be treated in accordance with the devices and methods provided herein by performing a transcatheter ablation procedure, including a pulmonary vein myocardium ablation procedure. In some embodiments, the ablation can be performed in temporal coordination with the delivery of a pharmacological agent to reduce the occurrence of vein stenosis or neointimal hyperplasia. In some embodiments, the pharmacological agent may be embodied in a coating on the surface of a balloon device that makes contact with the tissue receiving treatment. In particular embodiments, the pharmacological agent may be initially contained within a balloon device and then exuded through the surface of the balloon device to the tissue receiving treatment.

In general, one aspect of this document features a catheter-based medical device for treating a tissue. The device comprises an elongate catheter shaft including a liquid delivery lumen therethrough and a balloon device disposed at a distal end of the catheter shaft. The balloon device comprises an outer surface and an inner surface. The inner surface defines an interior space of the balloon device. The balloon device is in fluid communication with the liquid delivery lumen. The balloon device comprises a porous or microporous material that is arranged to transmit a liquid through the porous or microporous material. Additionally, one or more electrodes are disposed on or within the balloon device and are arranged to deliver energy to the tissue.

In various implementations, the one or more electrodes may be a single electrode disposed on said catheter shaft and in said interior space. The single electrode may be arranged to transmit radio frequency energy for ablation of the tissue. The one or more electrodes may be a plurality of electrodes disposed on the outer surface of the balloon device. The plurality of electrodes may comprise at least one electrode that is arranged to transmit radio frequency energy for ablation of the tissue and at least one electrode that is arranged to transmit direct current electrical energy. The one or more electrodes may comprise (i) a single electrode disposed on the catheter shaft and in the interior space and (ii) plurality of electrodes disposed on the outer surface. The single electrode may be arranged to transmit radio frequency energy for ablation of the tissue, and the plurality of electrodes may comprise at least one electrode that is arranged to transmit direct current electrical energy. The balloon device may have a generally cylindrical shape when the balloon is inflated. The balloon device may have a bulbous-shaped proximal portion and a generally cylindrical-shaped distal portion when the balloon is inflated. The bulbous-shaped proximal portion and the generally cylindrical-shaped distal portion may be in fluid communication. The balloon device may be arranged to completely occlude a left atrial appendage when the balloon is inflated.

In another general aspect, this document features a method for ablating a tissue of a patient. The method comprises inserting a catheter-based medical device into the patient; deploying the medical device near the tissue; supplying a pharmacological agent through the medical device; causing the pharmacological agent to exude from the medical device; and energizing at least a first one of one or more electrodes on the medical device. The energizing provides an energy sufficient for ablation of at least a portion of the tissue. The medical device comprises an elongate catheter shaft including a liquid delivery lumen therethrough; a balloon device disposed at a distal end of the catheter shaft, the balloon device comprising an outer surface and an inner surface, the inner surface defining an interior space of the balloon device, the balloon device in fluid communication with the liquid delivery lumen, the balloon device comprising a porous or microporous material that is arranged to exude a liquid through the porous or microporous material; and one or more electrodes that are disposed on or within the balloon device and are arranged to deliver energy to the tissue.

In various implementations, at least a portion of the energizing at least a first one of the one or more electrodes may take place while the pharmacological agent is exuding from the interior space to the outer surface. The pharmacological agent may transmit at least a portion of the energy sufficient for ablation of at least a portion of the tissue. The method may further comprise energizing at least a second one of the one or more electrodes, wherein the energizing comprises supplying direct current electricity energy sufficient for enhancing an uptake of the pharmacological agent by the tissue. The tissue may be a pulmonary vein. The tissue may be a renal artery. The pharmacological agent may be an antimitotic pharmacological agent. The tissue may be a left atrial appendage.

In another general aspect, this document features a catheter-based medical device for treating a tissue. The device comprises (i) an elongate catheter shaft including a liquid delivery lumen therethrough; (ii) a balloon device disposed at a distal end portion of the catheter shaft, the balloon device comprising an outer surface and an inner surface, the inner surface defining an interior space of the balloon device, the balloon device in fluid communication with the liquid delivery lumen, the balloon device comprising a porous or microporous material that is arranged to transmit a liquid through the porous or microporous material; (iii) one or more electrodes that are disposed on or within the balloon device and are arranged to deliver energy to the tissue; and (iv) a filter device, the filter device being deployable from the catheter shaft and generally coaxial with the balloon device, and wherein a distal end portion of the filter device is configured to contact a tissue surface surrounding the tissue.

In various implementations of the catheter-based medical device, the balloon device may be configured to extend distally of the filter device when the filter device and the balloon device are extended from the catheter shaft in a configuration to treat the tissue. The filter device may be a self-expanding device. The filter device may be arranged to be configured in a collapsed low-profile configuration and may reconfigure to an expanded configuration. The filter device may comprise a filter material having a pore size in the range of about 60 µm to about 120 µm, The filter device may comprise a mesh material that is disposed on a framework. The framework may comprise Nitinol. The filter device may be configurable in a collapsed low-profile configuration for containment within a lumen of the catheter shaft. The filter device may comprise one or more radiopaque markers. The balloon device may have a generally cylindrical shape when the balloon is inflated. The balloon device may have a bulbous-shaped proximal portion and a generally cylindrical-shaped distal portion when the balloon is inflated, and at least a portion of the filter device may be configured to surround the bulbous-shaped proximal portion when the filter device is in an expanded configuration. The filter device may be configured to substantially prevent blood from flowing through the filter device.

Particular embodiments of the subject matter described in this document can be implemented to realize one or more of the following advantages. Medical conditions such as atrial fibrillation, hypertension, and others can be effectively treated using the devices and methods provided herein. In some embodiments, atrial fibrillation can be treated by pulmonary vein ablation while preventing or reducing stenosis or neointimal hyperplasia of the pulmonary veins by providing a temporally coordinated delivery of an antimitotic pharmacological agent to the pulmonary vein during the ablation procedure. In some embodiments, the uptake of the antimitotic pharmacological agent to the tissue receiving the ablation treatment can be promoted using the methods and devices provided herein. In some embodiments, fibrosis can be advantageously promoted to treat various medical conditions. In some embodiments, embolic protection is provided by integrating a filter device with the ablation devices provided herein. In some embodiments, an occlusive member is integrated with the ablation devices to inhibit or prevent residual blood flow around or past the devices. In some such embodiments, the ablation treatment and/or the uptake of the antimitotic pharmacological agent to the tissue receiving the ablation treatment can be enhanced by substantially preventing blood flow around or past the devices. In some embodiments, various medical conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIGS. 2A-2C are schematic illustrations of balloon catheters that are capable of simultaneously delivering ablation energy and a stenosis prevention agent in accordance with some embodiments provided herein.

FIG. 2D is a schematic illustration of a balloon catheter with ablation electrodes on a first portion of the balloon and a drug coating on a second portion of the balloon.

Like reference numbers represent corresponding parts throughout.

DETAILED DESCRIPTION

Figure 1A:
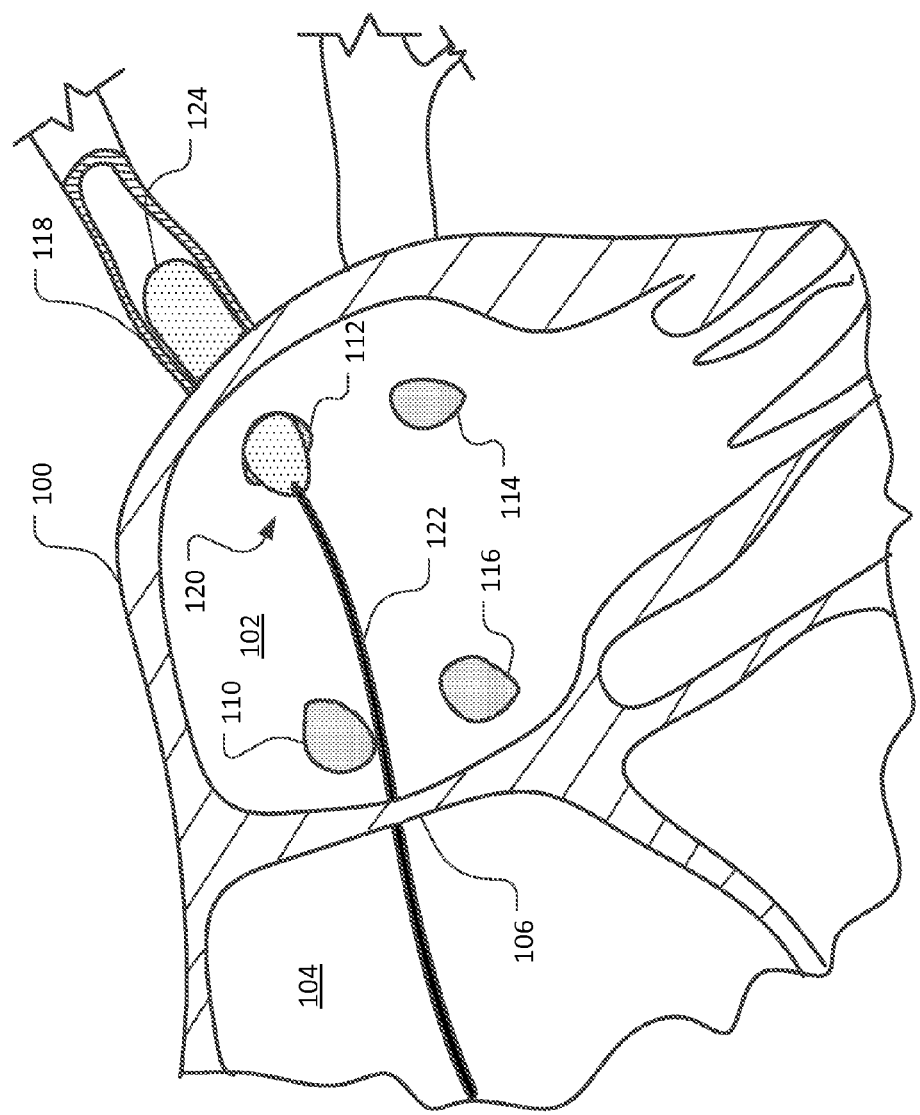
FIG. 1A is a schematic diagram of a heart undergoing a pulmonary vein ablation procedure using a catheter-based ablation device in accordance with some embodiments provided herein.

This document provides devices and methods for the treatment of heart conditions, hypertension, and other medical disorders. For example, among other things this document provides devices and methods for treating atrial fibrillation by performing a transcatheter pulmonary vein myocardium ablation procedure and for reducing the occurrence of vein stenosis or neointimal hyperplasia by delivering a pharmacological agent to the tissue receiving the ablative energy in temporal coordination with the ablative energy. In some implementations, the pharmacological agent is delivered simultaneously with the application of the ablative energy. In some implementations, the pharmacological agent is delivered before or after the application of the ablative energy. In some implementations, the pharmacological agent is delivered using a combination of such temporal methods. In some implementations, a repetitious cycling of such methods are used. However, in some implementations, no delivery of a pharmacological agent is administered directly by the ablation devices provided herein. Rather, in such implementations ablative energy is delivered without the delivery of a pharmacological agent from the ablation device.

While the devices and methods provided herein are primarily described in the context of the treatment of pulmonary veins to mitigate atrial fibrillation, many other bodily areas and medical conditions may be treated using the concepts provided. For example, the devices and methods provided herein may also be used to treat other thoracic veins, including the superior vena cava, left superior vena cava or its remnants, the azygos vein, and other venous structures. In another example, the devices and methods provided herein may also be used to treat the renal arteries as part of a renal denervation procedure. In addition, the devices and methods provided herein may also be used to treat bodily areas and medical conditions including but not limited to: pulmonary hypertension, appendage ablation; aortic coarctation; esophageal stenosis; bronchial tree, GI lumen and stenotic valve disorders; great vessel ablation for ventricular arrhythmia—as a handheld device for treating skin conditions including hemangiomas, burns, and wrinkles; the retroglossal region—to stiffen tissue and/or treat sleep apnea; peripheral vessels and coronary arteries—to "cholesterol proof" vessels and/or prevent atherosclerosis; gastric vessels or celiac—to lower ischemic threshold so satiety is felt earlier; coronary vessels—to treat vasospasm; heriorrhaphy or hernia repair, and cerebral vessels—to treat migraine.

Still further, the devices provided herein may be used for a preventative treatment for coronary atherosclerosis, especially in the left main, proximal LAD, and proximal circumflex That is, when used in combination with either a lipolytic agent or a calcilytic agent (e.g., diethyl ether) this technique can be used to treat coronary vascular legions. A further application of the devices and methods provided herein is retrouterine access to the fallopian tubes to treat stenosis, for example resulting from inflammatory disease, to keep the lumen open and the endothelium non-disrupted so that fertility is kept intact.

In addition, in some implementations the devices and methods provided herein can be used to treat certain conditions by ablating tissue while beneficially allowing or promoting a controlled and desirable level of fibrosis. In some implementations, a pharmacological agent that promotes fibrosis can be used. For example, urinary incontinence can be treated by fibrosing the urethral wall in a controlled manner. This technique can also be used to close lumens in some situations like diverticulae, aneurysms, and pseudoaneurysms. This technique can also be used to narrow or to completely sclerose the ostium of the left atrial appendage (LAA). In some cases, narrowing the ostium of the LAA will increase blood flow velocity thereby making stasis and thrombus less likely. Further, pulmonary bullae can also be treated by promoting fibrosis with an appropriate agent such as copper, and using a balloon device such as the example balloon device embodiments provided herein. In another example, varicose veins can be treated using a fibrosing agent combined with ablation energy to drive the agent into the vessel walls, in accordance with the devices and methods provided herein.

Further, in some implementations the devices and methods provided herein can be used to abate the development of atheroma within arterial vessels. That is, in some cases the negative effects of cholesterol in the coronary arteries or major vasculature can be reduced. In some implementations, the devices and methods provided herein can be used to stabilize existing atheroma, thereby making rupture of atheroma less likely.

In general, the concepts disclosed herein provide to a target area of the body the temporally coordinated delivery of: (i) tissue-ablative energy and, in some embodiments (ii) an antimitotic/antifibrotic pharmacological agent to abate the generation of stenosis and neointimal hyperplasia that may be caused by the delivery of the tissue-ablative energy. For example, this document discloses a variety of multi-functional balloon catheter embodiments, and methods for their use. These balloon catheters include one or more ablative energy sources, as well as the ability to deliver a pharmacological agent (in some embodiments) for the prevention or reduction of vessel stenosis and neointimal hyperplasia. Those device embodiments that are capable of delivering a pharmacological agent may do so using a variety of delivery modalities. For example, in some embodiments the pharmacological agent may be embodied in a coating on the surface of a balloon device that makes contact with the tissue receiving treatment. In particular embodiments, the pharmacological agent may be initially contained within a balloon device and then exuded through the porous or microporous surface of the balloon device to the tissue receiving treatment. In other device embodiments described below (refer to FIGS. 5A, 5B, 6A, and 6B), an expandable tubular framework with surface electrodes is used to deliver ablation energy to target tissue. In some such embodiments, the tubular framework can be used as conduits) to convey a pharmacological agent to the tissue.

The coordinated delivery of ablative energy and anti-stenosis drugs can enable an effective treatment of atrial fibrillation and other medical conditions. One contributing factor to the efficacy of the treatment is that it can allow the entire circumference of the pulmonary veins and/or pulmonary vein ostia to be ablated with a lessened potential of causing pulmonary vein stenosis. In contrast, some other ablation procedures ablate only a partial circumference of the pulmonary veins to reduce the potential of causing pulmonary vein stenosis. Such partial-circumferential ablation procedures may have a lower efficacy of treating atrial fibrillation. However, because of the delivery of the anti-stenosis pharmacological agent along with the ablation energy, an entire circumference of the pulmonary veins and or pulmonary ostia can be ablated using the devices and methods provided herein.

While the embodiments described herein are disclosed as providing specific types of ablation, it should be understood that a variety of ablation techniques and ablative energy sources are envisioned for use in combination with any of the devices provided herein. For example, monopolar or bipolar ablation techniques can be used. Ablation energy sources such as radiofrequency (RF), direct current (DC), alternating current (AC) in non-cardiac applications, cryogenics, hot solutions, and the like, and combinations thereof, can be used with the devices provided herein. In some embodiments, both DC and RF electrodes can be advantageously used in combination on the balloon devices provided herein. That is, RF electrodes may be included because they are well-suited for delivering ablation energy, while DC electrodes may also be included because they are well-suited as iontophoretic sources for driving the pharmacological agents into tissue. The use of DC and RF electrodes in combination can thereby provide a device that provides the benefits of both types of electrodes. In some embodiments, the same energy source used for ablation can be used to drive the medication/antifibrotic agent into the tissue. However, in some embodiments DC and a magnet-driven gradient can be used to drive the particles into the tissue as well. The carrier molecule for the antifibrotic agent may serve as an elution agent as well as a reservoir so that there is a long-term deployment of a stenosis-preventing agent. This may also enable noninvasive ablation by targeting the metallic particles that were driven into the vessel wall.

In some embodiments, the electrodes for delivery of the ablation energy are located on the exterior surface of the ablation devices. In other embodiments, one or more central electrodes are located on a central shaft within the interior space of a balloon ablation device. In those cases, in some embodiments the energy from the central electrode(s) can be transmitted to the target tissue by the liquid pharmacological agent that bathes the central electrode(s) and that exudes, elutes, weeps, or is otherwise transmitted from within the balloon to the tissue outside of the balloon. In some embodiments, a combination of types of electrodes are included in a single balloon device.

Another balloon embodiment has spikes or spindles on the balloon's outer surface that are arranged to wedge into the surrounding tissue such as myocardial tissue. These spikes or spindles can be metallic or made of the same material as the balloon itself. Some such embodiments have a balloon in a balloon, with the inside balloon being used to push the spindles out into the vessel or viscous tissue wall.

Another balloon embodiment has a natural (inflated) shape that is configured to be placed in the left atrial appendage. An ablation can be performed on a wide ring at the ostium of the appendage to electrically isolate the appendage in a simple, straightforward manner. When the balloon is still inside the appendage it is used as a marker. Epicardial access can be attained and clip electrodes can be placed on the left atrial appendage, as well as the right atrial appendage. This technique provides a stroke prevention therapy where the appendages will be stimulated, but because they are isolated, even if atrial fibrillation were to occur, the atrium will not fibrillate. This technique may provide the benefit that the muscle of the appendage can still be utilized to contribute to left atrial filling, which in turn may contribute to left ventricular filling, despite the presence of atrial fibrillation.

Another balloon embodiment includes an inner balloon within an outer balloon. A lumen of a catheter shaft is in fluid communication with the inter-balloon space between the inner and outer balloon. A drug can be delivered through the lumen and into the inter-balloon space. In coordination with the delivery of the drug, electrical or other types of energy can be delivered at a surface of either or both of the balloons, or at a location therebetween via electrodes within the inter-balloon chamber. Such a design can also advantageously allow different design and performance characteristics for the two balloons.

Another balloon embodiment can have electrodes placed on the balloon for recording and pacing, both proximally and distally, as well as along the balloon's length. This arrangement can advantageously enable the use of algorithms that employ impedance measurements and electrogram-derived signals to preferentially deliver dosages of the drug in relation to deliveries of the energy and vice versa (e.g., more energy at certain electrogram sites and more drug at other sites).

Another catheter-style ablation device provided herein includes, in addition to a balloon device, a framework or scaffolding member that is disposed on a central catheter along with the balloon device. The framework can be expandable (e.g., made from a super-elastic material such as, but not limited to, nitinol) and can have ablation electrodes disposed on the framework. In some embodiments, the framework is tubular. In particular embodiments, the tubular framework can be used as conduit(s) to convey a pharmacological agent to the tissue site that receives ablation treatment from the electrodes on the framework.

The embodiments described herein include provisions for the exudation and elution of a liquid pharmacological agent for the prevention or reduction of vessel stenosis and neointimal hyperplasia. For instance, the drug paclitaxel is an example of one type of an antimitotic pharmacological agent that can be delivered to the tissue undergoing ablation to prevent or reduce fibrosis and stenosis of the tissue. Paclitaxel can be used beneficially because of its rapid uptake and prolonged retention. In some implementations, paclitaxel can be delivered in 3% saline (or similar hypertonic solution) to further enhance its uptake and retention. While paclitaxel is provided as an example, other pharmacological agents can also be used. In some implementations, fine metal components (e.g., gold or tungsten) can be combined with the liquid pharmacological agents to form a barrier thereby preventing the agent from leaking out of the tissue. In other implementations, a high-energy DC shock (e.g., about 2 to 250 Joules) can be applied to the tissue during and/or after exuding the agent to effectively push the agent into the tissue.

The balloon devices provided herein can include materials of construction that are porous or microporous. As such, the balloons can allow exudation, elution, or weeping of liquid pharmacological agents from within the interior space of the balloon to the exterior surface of the balloon. In some embodiments, the balloon can comprise a balloon within a balloon, with the liquid pharmacological agent disposed in the cavity between the two balloons. This configuration can be used, for example, to reduce the required volume of liquid pharmacological agent within the balloon device. In some embodiments, the balloon devices provided herein, as an alternative to or in addition to being porous, can be coated with a pharmacological agent. Such coatings can be disposed on the surface of the balloon to make contact with the tissue, or near the tissue, that receives ablative energy from the electrodes of the balloon devices. The pharmacological agent coated on the balloon surface can thereby transfer to the tissue to provide a therapeutic effect.

FIG. 1A is a schematic diagram of a heart 100 undergoing a pulmonary vein ablation procedure using a balloon catheter device 120 in accordance with some embodiments provided herein. In general, balloon catheter device 120 includes a multi-lumen catheter shaft 122 connected to a balloon device 124. The proximal end of balloon catheter device 120 is connected to an ablation energy source and controller (e.g., an RF generator system not shown) and a liquid pharmacological agent source (not shown), both of which are located external to the patient. Balloon device 124 is located at the distal end of catheter shaft 122. An interior space of balloon device 124 is in fluid communication with a liquid delivery lumen of catheter shaft 122. The liquid delivery lumen is used to convey the liquid pharmacological agent from the source external to the patient into the interior space of balloon device 124.

The distal end of balloon catheter device 120 can be positioned in a left atrium 102 of heart 100 according to standard techniques. For instance, using an example standard technique balloon catheter device 120 can enter a right atrium 104 of heart 100 through a femoral vein and the inferior vena cava (not shown). Balloon catheter device 120 can pass through a puncture in an atrial septum 106 to access left atrium 102. From left atrium 102, balloon catheter device 120 can pass through any of the pulmonary vein ostia 110, 112, 114, or 116 to enter a pulmonary vein such as pulmonary vein 118 shown. In some cases, balloon catheter device 120 can be an over-the-wire device that is delivered over or on a pre-placed guidewire. In some cases, a delivery catheter/sheath is used to assist in the insertion and placement of balloon catheter device 120 (refer to FIGS. 2A-2C). In some cases, one or more radiopaque markers can be included on balloon catheter device 120 to assist with the radiographical visualization of the position of balloon catheter device 120 during delivery and deployment.

With balloon catheter device 120 positioned within pulmonary vein 118, balloon device 124 can be inflated using a liquid pharmacological agent as the inflation medium. The inflation of balloon device 124 will cause the outer surface of balloon device 124 to make contact with the inner wall of pulmonary vein 118. In addition, the pressure of the liquid pharmacological agent inflation medium will cause some of the agent to exude, elute, weep, or otherwise be transmitted from within the interior space of the balloon 124 to the exterior surface of the balloon 124, and into contact with the inner wall of pulmonary vein 118. At this juncture, balloon catheter device 120 can be energized with ablation energy to initiate the modulation of target neural fibers.

An example ablation technique can be generally performed as follows. An electric field can be generated by the external source/controller and transferred through wires within one or more lumens of catheter shaft 122 to electrodes disposed on the surface of or within balloon device 124. The electric energy can be transmitted to the inner wall of pulmonary vein 118 directly from the electrodes on the surface of balloon device 124 or from the electrodes within balloon device 124 via the liquid pharmacological agent that exudes from the exterior surface of balloon device 124. The electric field can modulate the activity along neural fibers within the wall of pulmonary vein 118 by at least partially denervating the tissue. In some examples, while the electric field for ablation is being applied, transmission of the liquid pharmacological agent from balloon device 124 to the tissue can be continued.

The ablation process can be performed simultaneously and concurrently with the delivery of an antimitotic pharmacological agent to the tissue receiving the ablation energy. Alternatively, the ablation process can be performed sequentially with the delivery of an antimitotic pharmacological agent to the tissue receiving the ablation energy. That is, the antimitotic pharmacological agent can be delivered first and the ablation process can take place thereafter. Or, the antimitotic pharmacological agent can be delivered after the ablation process. In some implementations, a combination of such techniques can be used. For example, the antimitotic pharmacological agent can be delivered before and during the ablation process, or before and after, and so on. In other embodiments, the balloon 124 is coated with a pharmacological agent that is absorbed into the tissue of the pulmonary vein 118. In still other procedures, no pharmacological agent is administered directly by the balloon catheter device 120.

Such techniques for the coordination of the deliveries of the ablative energy and the pharmacological agents can provide advantageous results. For example, delivering the agent prior to the ablative energy can provide iontophoresis-like action to drive the agent farther into the tissue. In another example, delivering the ablative energy prior to the pharmacological agent can provide some electroporative disruption of the endothelial cell-to-cell junction, thus promoting the agent delivery. In some implementations, a repetitious cyclic delivery of ablative energy and the pharmacological agent can thereby further enhance uptake of the agent. In some implementations, the pharmacological agent can have an ionic base so as to optimize the ablative energy's ability to get the agent beyond the endothelium of the tissue.

Paclitaxel is an example of one type of antimitotic pharmacological agent that is well-suited for this application. This technique of coordinating the delivery of paclitaxel with the ablation process can prevent or reduce the occurrence of fibrosis, stenosis, and neointimal hyperplasia of the tissue undergoing ablation. In such fashion, stenosis of pulmonary vein 118 can be reduced or prevented while full-circumferential ablation of pulmonary vein 118 is performed.

Figure 1B:
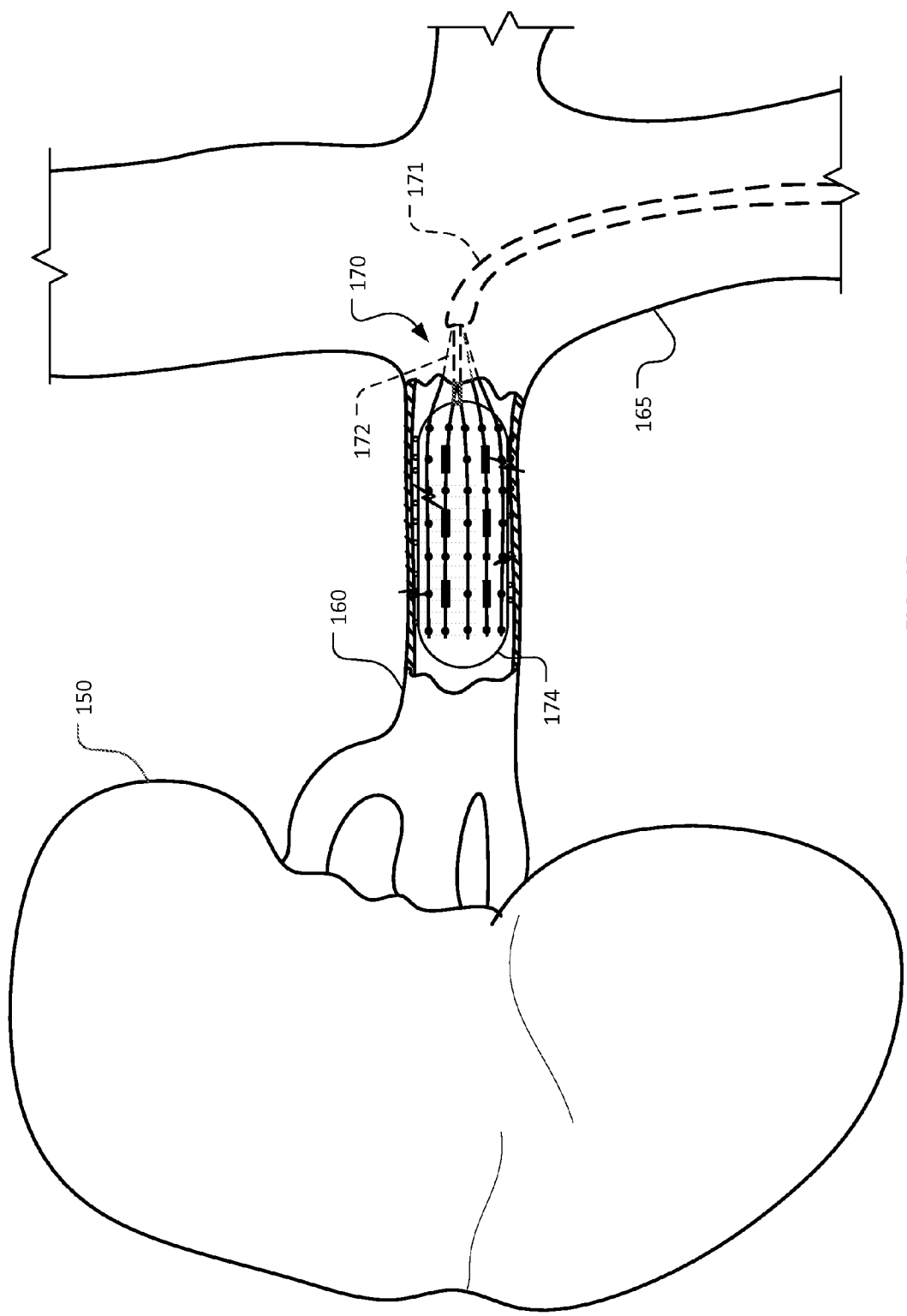
FIG. 1B is a schematic diagram of renal artery undergoing an ablation procedure using a catheter-based ablation device in accordance with some embodiments provided herein.

FIG. 1B is a schematic diagram of a kidney 150 and a renal artery 160 undergoing an ablation procedure using a balloon catheter device 170 in accordance with some embodiments provided herein. In the depicted implementation, the balloon catheter device 170 was directed to the site of the renal artery 160 via the femoral artery and the aorta 165 using a delivery sheath 171. However, other approaches may also be used. In general, balloon catheter device 170 includes a multi-lumen catheter shaft 172 that is coupled to a balloon device 174. The proximal end of balloon catheter device 170 is connected to an ablation energy source and controller (e.g., an RF generator system, not shown) and a liquid pharmacological agent source (not shown), both of which are located external to the patient. Balloon device 174 is located at the distal end of catheter shaft 172. An interior space of balloon device 174 is in fluid communication with a liquid delivery lumen of catheter shaft 172. In this embodiment, the liquid delivery lumen is used to convey the liquid pharmacological agent from the source external to the patient into the interior space of balloon device 174. In alternative embodiments, the balloon device 174 can be coated with a pharmacological agent. In still other embodiments, no pharmacological agent is so used.

With balloon catheter device 17 positioned within renal artery 160, in some embodiments balloon device 174 can be inflated using a liquid pharmacological agent as the inflation medium. In alternative embodiments, other inflation media can be used such as, but not limited to, saline, air, or carbon dioxide. The inflation of balloon device 174 will cause the outer surface of balloon device 174 to make contact with the inner wall of renal artery 160. In addition, in embodiments so configured, the pressure of the liquid pharmacological agent inflation medium will cause some of the pharmacological agent to exude, elute, weep, or otherwise be transmitted from within the interior space of the balloon 174 to the exterior surface of the balloon 174, and into contact with the inner wall of renal artery 160. At this juncture, (or before, or during such transmission, or using a combination of such techniques) balloon catheter device 170 can be energized with ablation energy to initiate the modulation and denervation of target neural fibers.

In some embodiments, the ablation process of renal artery 160 can be performed simultaneously and concurrently with the delivery of an antimitotic pharmacological agent to the tissue receiving the ablation energy. Alternatively, the ablation process can be performed sequentially with the delivery of an antimitotic pharmacological agent to the tissue receiving the ablation energy. That is, the antimitotic pharmacological agent can be delivered first and the ablation process can take place thereafter. Or, the antimitotic pharmacological agent can be delivered after the ablation process. In some implementations, a combination of such techniques can be used. For example, the antimitotic pharmacological agent can be delivered before and during the ablation process, or before and after, and so on. In other embodiments, balloon 174 is coated with a pharmacological agent that is absorbed into the tissue of renal artery 160. In still other procedures, no pharmacological agent is administered using balloon catheter device 170.

Figure 1C:
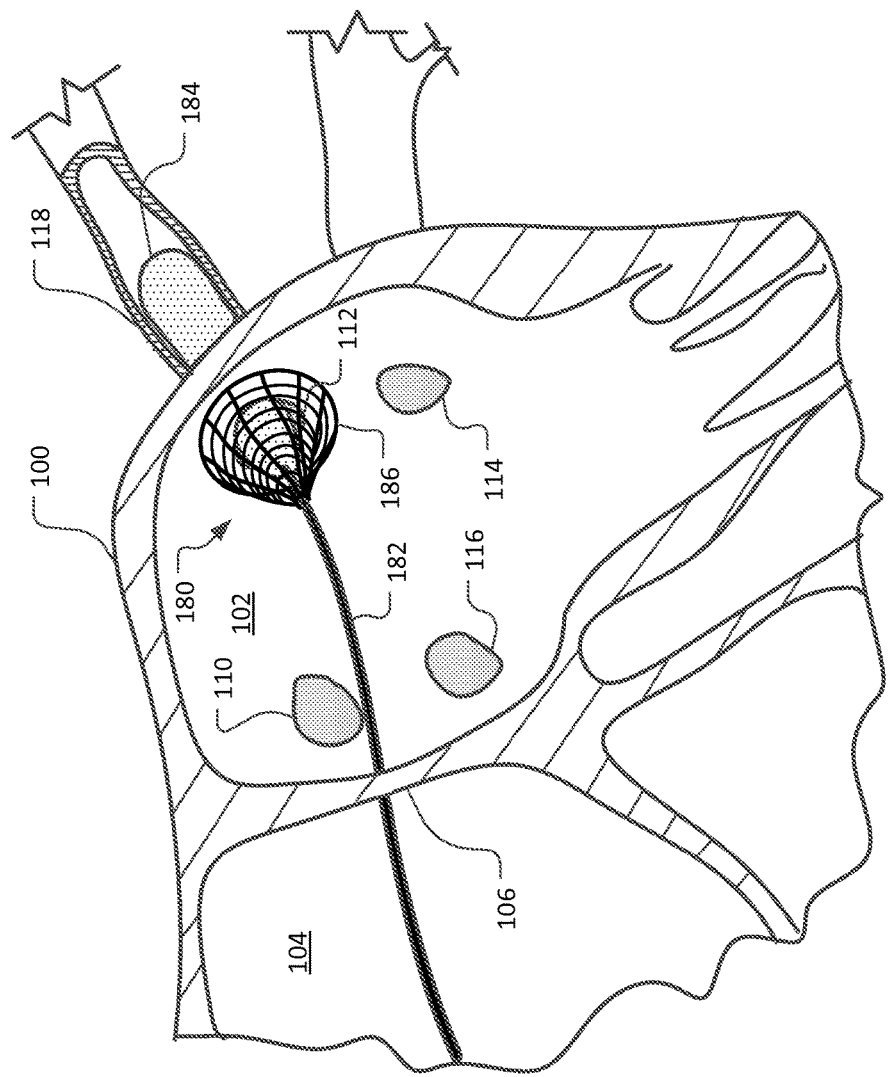
FIG. 1C is the schematic diagram of FIG. 1A showing the use of another embodiment of a catheter-based ablation device.

FIG. 1C is a schematic diagram of the heart 100 undergoing a pulmonary vein ablation procedure using another example balloon catheter device 180 in accordance with some embodiments provided herein. In general, balloon catheter device 180 includes a multi-lumen catheter shaft 182, a balloon device 184, and a filter device 186. The proximal end of balloon catheter device 180 is connected to an ablation energy source and controller (e.g., an RF generator system not shown) and a liquid pharmacological agent source (not shown), both of which are located external to the patient.

In an arrangement that is analogous to that of balloon catheter device 120 described above, balloon device 184 is located at the distal end of catheter shaft 182. An interior space of balloon device 184 is in fluid communication with a liquid delivery lumen of catheter shaft 182. The liquid delivery lumen is used to convey the liquid pharmacological agent from the source external to the patient into the interior space of balloon device 184.

With balloon catheter device 180 positioned within pulmonary vein 118, balloon device 184 can be inflated using a liquid pharmacological agent as the inflation medium. The inflation of balloon device 184 will cause the outer surface of balloon device 184 to make contact with the inner wall of pulmonary vein 118. In addition, the pressure of the liquid pharmacological agent inflation medium will cause some of the agent to exude, elute, weep, or otherwise be transmitted from within the interior space of balloon 184 to the exterior surface of balloon 184, and into contact with the inner wall of pulmonary vein 118. At this juncture (or at another time in relation to the transmission of the liquid pharmacological agent from balloon 184), balloon catheter device 180 can be energized with ablation energy to initiate the modulation of target neural fibers.

In some embodiments, balloon catheter device 180 also includes filter device 186. In some embodiments, filter device 186 can be a discrete catheter device that can be deployed from a delivery sheath (e.g., multi-lumen catheter shaft 182) to encapsulate the area around pulmonary vein ostia 112 containing balloon 184, as well as for other suitable uses. In some embodiments, filter device 186 includes a central aperture or tube through which other devices (e.g., balloon device 184) can be extended/translated. In alternative embodiments, filter device 186 can be integrated with multi-lumen catheter shaft 182.

In some embodiments, filter device 186 is contained within multi-lumen catheter shaft 182 in a collapsed low-profile delivery configuration during navigation of balloon catheter device 180 to the target site. At the target site, filter device 186 can be deployed, that is, made to emerge from multi-lumen catheter shaft 182. Filter device 186 may be deployed before the deployment of balloon 184 in some embodiments. However, in some embodiments, filter device 186 may be deployed after the deployment of balloon 184. In still other embodiments, filter device 186 may be deployed essentially simultaneously with balloon 184.

In some embodiments, filter device 186 is self-expanding to enlarge to a size and shape so as to encapsulate the area around pulmonary vein ostia 112. That is, as filter device 186 is made to emerge from or extend from multi-lumen catheter shaft 182, in some embodiments filter device 186 will be biased to reconfigure from the low-profile delivery configuration to an expanded configuration.

In some embodiments, the expanded configuration of filter device 186 is generally conical. However, the conical shape is not required. In some embodiments, filter device 186 may expand to other shapes such as, but not limited to, pyramidal, cylindrical, frustoconical, and the like. Filter device 186 is configured to maintain full-wall apposition against the topography defined by the tissue surrounding pulmonary vein ostia 112.

Filter device 186 is configured to provide embolic protection. For example, filter device 186 can capture blood clots, plaque, tissue fragments, shards or particles of pharmacological agents, and the like. In some circumstances, some such emboli may be generated or may become embolic as a result of the use of balloon catheter device 180.

After the desired treatment is provided by balloon catheter device 180, filter device 186 can be reconfigured back to the collapsed low-profile configuration for removal from the patient. Filter device 186 is configured so that, as filter device 186 is collapsed, any emboli present therein remain securely contained within the collapsed filter device 186.

Filter device 186 can be constructed of various materials and configurations, and can be constructed using various techniques. In some embodiments, filter device 186 comprises a mesh material. In some such embodiments, the mesh material can comprise a Nitinol material. In some such embodiments, the filter device 186 comprises a polyester mesh material, a polyurethane mesh material, or another type of synthetic material.

In some embodiments, filter device 186 can comprises a framework of struts and one or more loops. In some embodiments, the framework can be constructed of Nitinol, or another material. A mesh material can be disposed on the framework. For example, in some embodiments a polyester mesh material can be disposed on a Nitinol framework. In some such embodiments, a compliant nitinol ring on the distal end of the filter device 186 can be used to support the filter material and to mold against the topography of the tissue surrounding the pulmonary vein ostia 112.

The pore size of the filter device 186 can be selected as desired to provide the desired embolic protection while allowing the transmission of blood flow therethrough. For example, in some embodiments the filter device may have a pore size in the range of about 40 µm to about 60 µm, about 50 µm to about 70 µm, about 60 µm to about 80 µm, about 70 µm to about 90 µm, about 80 µm to about 100 µm, about 90 µm to about 110 µm, about 100 µm to about 120 µm, about 110 µm to about 130 µm, about 120 µm to about 140 µm, about 130 µm to about 150 µm, about 140 µm to about 160 µm, or greater than 160 µm.

In some embodiments, filter device 186 can additionally or alternatively be configured to substantially occlude blood flow around the region of balloon 184 and pulmonary vein ostia 112. In some such embodiments, the pore size of filter device 186 can be selected so that filter device 186 will occlude all or substantially all blood flow therethrough. In this manner, blood flowing between balloon 184 and the inner wall of pulmonary vein 118 can be reduced or eliminated as desired. Similarly, blood flowing in the space between filter device 186 and pulmonary vein ostia 112 can be reduced or eliminated as desired. By so controlling the blood flow using filter device 186, the therapeutic efficacy of balloon catheter device 180 can be enhanced in some circumstances. For example, in some circumstances the uptake of liquid pharmacological agents and/or the transfer of ablation energy from balloon catheter device 180 to the surrounding tissue can be enhanced by controlling the blood flow using filter device 186.

In some embodiments, portions of the filter device 186 can be enhanced to provide radiographic visualization of the position and orientation of the filter device 186. For example, some embodiments include a loop of radiopaque material (e.g., titanium, tungsten, barium sulfate, zirconium oxide, and the like) around the mouth of the filter to allow for precise positioning and verification of apposition before proceeding with the intervention. Alternatively, or additionally, in some embodiments one or more radiopaque markers can be included on other portions of filter device 186.

With reference to FIGS. 2A-2C, example embodiments of catheter-based balloon ablation devices 200, 240, and 280 are provided. These device embodiments are arranged to coordinate the delivery of tissue ablation energy and a liquid pharmacological agent to the tissue receiving the ablation energy. While the embodiments depicted are generally cylindrical, other shapes and a range of sizes are also envisioned to adapt the devices to the various applications described herein. It should be understood that other embodiments of catheter-based balloon ablation devices may be coated with a pharmacological agent. In still other embodiments, the catheter-based balloon ablation devices provided herein may be used without the administration of any pharmacological agent that is administered directly by the balloon ablation device.

It should also be understood, that the features and usage techniques described herein in relation to the various ablation devices can be combined with the features of other ablation device embodiments and usage techniques described herein. Accordingly, based on such combinations and sub-combinations, an extensive number of ablation device embodiments and usage techniques are envisioned and provided herein.

FIG. 2A depicts a balloon catheter ablation device 200 that includes a catheter shaft 222 and a balloon device 224 that is disposed on the distal end of catheter shaft 222. Balloon device 224 is shown in an axial cross-sectional view to provide enhanced visualization of its interior space.

Balloon device 224 is shown in its inflated configuration, but balloon device 224 can be inflated and/or deflated as desired by a clinician operator. In general, during insertion and placement within a patient, balloon device 224 is in its deflated configuration. When deflated, balloon device 224 can be positioned within a low-profile delivery catheter 223. When the distal tip of delivery catheter 223 is located in a desired anatomical position within the patient, catheter shaft 222 can be moved distally in relation to delivery catheter 223 to make balloon device 224 emerge from the distal tip of delivery catheter 223. Balloon device 224 can then be inflated to make contact with the tissue of the patient, such as within a pulmonary vein (refer to FIG. 1).

An antimitotic pharmacological agent 230, such as paclitaxel, can be used as the inflation medium. Pharmacological agent 230 can be delivered from a source (not shown) located external to the patient, through a lumen in catheter shaft 222, and into the interior space of balloon device 224 through ports 226a-b located on catheter shaft 222 inside balloon device 224. In some embodiments, one inflation medium delivery port is included on catheter 222, but in other embodiments three or more ports are included. Pharmacological agent 230 can pressurize the interior space of balloon device 224 to cause balloon device 224 to inflate to the generally cylindrical configuration shown.

The material of balloon device 224 can be porous or microporous. As such, antimitotic pharmacological agent 230 can elute, exude, or weep from the interior of balloon device 224 to its exterior, as depicted by the multiple droplets 232. From the position on the exterior of balloon device 224, droplets 232 can contact the surrounding tissue (e.g., pulmonary vein 118 as shown in FIG. 1). The tissue can absorb droplets 232, which can prevent or reduce fibrosis, stenosis, and neointimal hyperplasia of the tissue.

Catheter shaft 222 can include an axial electrode 234 for the delivery of ablation energy. Electrode 234 can be electrically wired to an ablative energy source (not shown) located external to the patient. For example, in some embodiments an RF energy source can be used. In other embodiments, other types of energy can be used (e.g., DC, AC, cryogenic, and the like). In some embodiments, a combination of such energy sources can be used within a single embodiment of ablation balloon device (e.g., RF and DC are used in combination is some embodiments). The ablation energy can be monopolar or bipolar.

In some embodiments, balloon catheter ablation device 200 can delivery ablation energy to surrounding tissue as follows. Electrical current can transfer from axial electrode 234 to pharmacological agent 230 as depicted by electrical symbols 235. In turn, electrical current can transfer from droplets 232 of pharmacological agent 230 to surrounding tissue as depicted by electrical symbols 236. In this fashion, delivery of ablation energy 236 and antimitotic pharmacological agent 230 can take place simultaneously from balloon ablation device 200 to surrounding tissue.

With reference to FIG. 2B, an example balloon catheter ablation device 240 includes multiple electrodes 250 and 260 that are provided on the surface of balloon device 224. In some embodiments, electrodes 250 and 260 can be different types of electrodes, and/or electrodes 250 and 260 can be configured to deliver different types of energy. For example, in the embodiment of FIG. 2B electrodes 260 are DC electrodes and electrodes 250 are RF electrodes. DC electrodes 260 can provide DC electrical current 262, which can be well-suited to helping facilitate the uptake of droplets 232 of pharmacological agent 230 into surrounding tissue. RF electrodes 250 can provide RF energy 252, which can be well-suited to causing ablation and denervation of surrounding tissue.

The electrodes 250 and/or 260 can be individual electrodes (i.e., having individual contacts with a generator/controller device), segmented electrodes with two or more commonly connected contacts, or single continuous electrodes with a common contact. In some embodiments, the electrodes 250 and/or 260 may be configured to provide a bipolar signal. In some embodiments, electrodes 250 and/or 260 may be used, together or individually, in conjunction with a separate patient ground pad for monopolar use. Balloon device 224 and catheter shaft 222 are described in reference to FIG.

2A. That is, balloon device 224 can provide antimitotic pharmacological agent 230 delivered from catheter shaft 222 to surrounding tissue in droplets 232. At the same time (if desired), or before or after delivery of the agent 230, electrodes 250 and 260 can be activated to provide energy 252 and 262 to surrounding tissue. In this fashion, delivery of ablation energy 252 and antimitotic pharmacological agent droplets 232 can take place in a coordinated fashion from balloon catheter ablation device 240 to surrounding tissue.

With reference to FIG. 2C, an example balloon catheter ablation device 280 includes DC electrodes 260 that are provided on the exterior surface of balloon device 224 and an RF axial electrode as described in reference to FIG. 2A. Balloon device 224 and catheter shaft 222 are also described in reference to FIG. 2A. Ablation energy 236 can be delivered to surrounding tissue from the internal RF axial electrode via the droplets 232 of antimitotic pharmacological agent 230. DC energy can be provided from surface electrodes 260 to help facilitate the uptake of droplets 232 of pharmacological agent 230 into surrounding tissue. In this fashion, delivery of ablation energy 236 and antimitotic pharmacological agent droplets 232 can take place simultaneously or in a sequentially coordinated manner from balloon ablation device 280 to surrounding tissue.

With reference to FIG. 2D, an example of another embodiment of a balloon catheter ablation device 290 includes an ablation portion 294 and an antimitotic pharmacological agent delivery portion 295 on a single balloon device 292. In this embodiment, ablation portion 294 is located proximally of antimitotic pharmacological agent delivery portion 295. In alternative embodiments, ablation portion 294 can be located distally of antimitotic pharmacological agent delivery portion 295. In some embodiments, antimitotic pharmacological agent delivery portion 295 is a drug-coated portion of balloon device 292. In other embodiments, balloon device 292 can be partly or fully made from a porous or microporous material, and an antimitotic pharmacological agent can be supplied as an inflation fluid such that the pharmacological agent can elute, weep, or be otherwise transmitted through balloon device 292 to the tissue.

In one example implementation of balloon catheter ablation device 290, ablation portion 294 is first positioned adjacent to the target tissue. Catheter shaft 222 can be used to move balloon device 292 proximally and distally as desired. Balloon device 292 can then be inflated with an inflation fluid such that electrodes 260 make contact with the tissue. Ablation energy 262 can then be provided from electrodes 260 to the tissue. After delivery of ablation energy 262 as desired, the inflation fluid can be at least partially removed from balloon device 292 to reduce the outer diametrical size of balloon device 292. Using catheter shaft 222, balloon device 292 can then be retracted proximally so that antimitotic pharmacological agent delivery portion 295 is approximately in position to make contact with the tissue that received ablation energy 262. Then inflation fluid can again be supplied to balloon device 292 such that the surface of antimitotic pharmacological agent delivery portion 295 makes contact with the ablated tissue. The antimitotic pharmacological agent can thereby be transferred to the tissue. That is, in embodiments that have an antimitotic pharmacological agent coated on the surface of antimitotic pharmacological agent delivery portion 295, the contact between the coating and the tissue can facilitate transfer of the pharmacological agent to the tissue. In other embodiments, balloon device 292 can be partly or fully made from a porous or microporous material, and the antimitotic pharmacological agent can elute, weep, or be otherwise transmitted through balloon device 292 to the tissue.

Figure 3A:
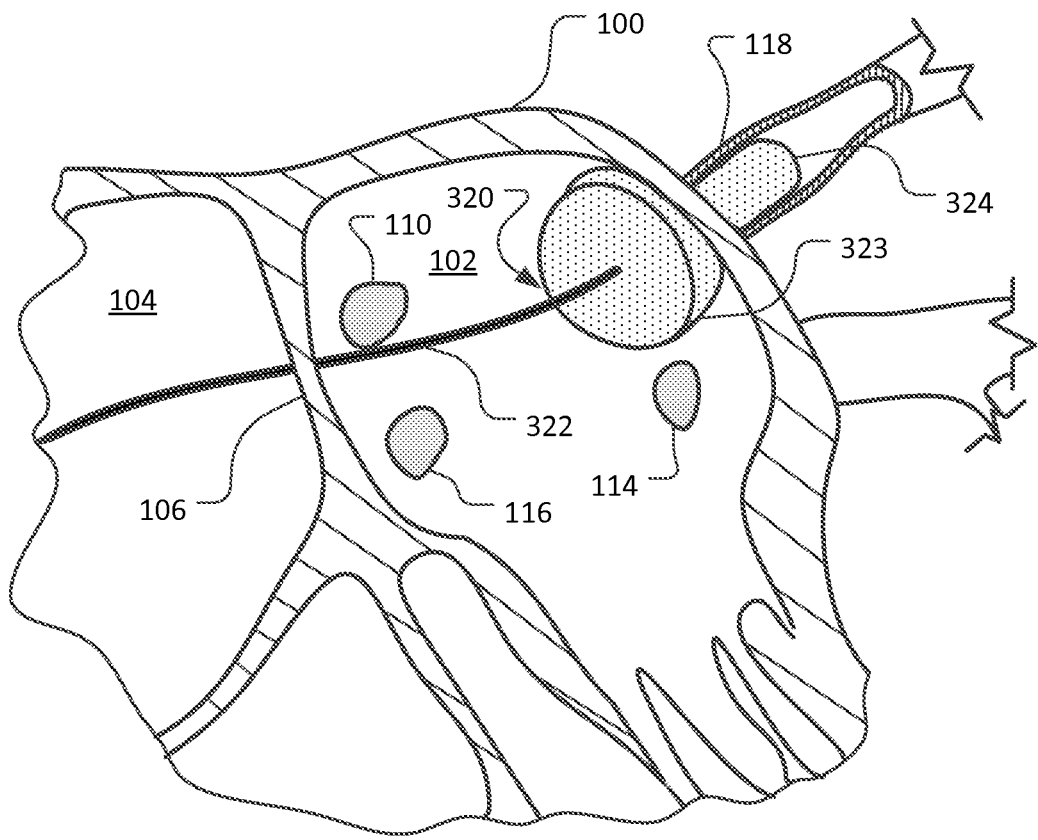
FIG. 3A is a schematic diagram of heart undergoing a pulmonary vein ablation using another catheter-based device in accordance with some embodiments provided herein.

With reference to FIG. 3A, heart 100 is depicted as receiving an ablation procedure using an example balloon catheter ablation device 320. Balloon catheter ablation device 320 is similar to other balloon catheter ablation devices described herein but with the addition of a bulbous proximal balloon portion 323 that contacts and delivers ablation energy to the tissue surrounding the ostium of pulmonary vein 118.

Figure 3B:
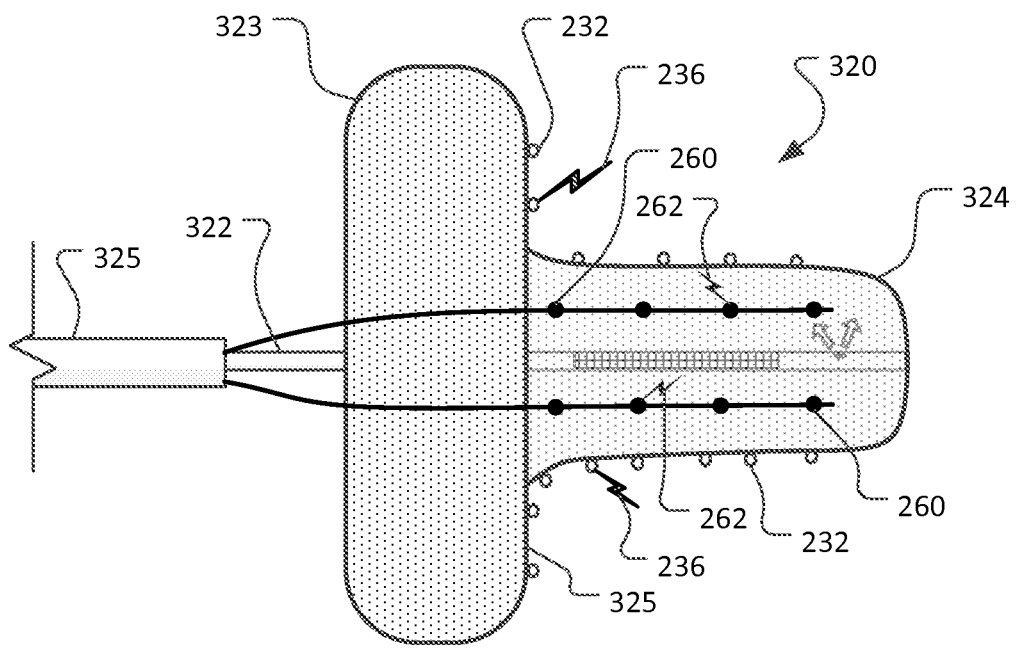
FIG. 3B is a schematic illustration of another balloon catheter that is capable of simultaneously delivering ablation energy and a stenosis prevention agent in accordance with some embodiments provided herein.

FIG. 3B illustrates balloon catheter ablation device 320, including its distal generally cylindrical balloon portion 324 in addition to bulbous proximal balloon portion 323. In some embodiments, the balloon portions 323 and 324 are in fluid communication with each other to provide a single balloon interior space. In alternate embodiments, the balloon portions 323 and 324 have separated volumetric spaces that are each supplied with inflation fluid from individually discrete lumens in catheter shaft 322. In still other embodiments, a single lumen supplies both balloon portions 323 and 324, but as inflation fluid is supplied, cylindrical balloon portion 324 inflates first and bulbous proximal balloon portion 323 inflates after the time at which cylindrical balloon portion 324 is substantially inflated or nearly substantially inflated.

A liquid antimitotic pharmacological agent can be delivered via catheter shaft 322 to inflate balloon portions 323 and 324. Pharmacological agent droplets 232 can form on the exterior surfaces of either or both of balloon portions 323 and 324 that are in contact with surrounding tissue. Electrodes 260 can deliver DC energy 262 to help facilitate uptake of pharmacological agent droplets 232 by surrounding tissue. Ablation energy can be delivered in various ways. In some embodiments, a central axial electrode is included on catheter shaft 322 to electrify the droplets 232 as depicted by electrical symbols 236. In some embodiments, surface electrodes (e.g., RF electrodes) can be located on the surface of balloon portions 323 and/or 324. In some embodiments, such surface electrodes can be located on the distal face 325 of bulbous proximal balloon portion 323 that contacts the myocardial tissue at the circumferential margin of pulmonary vein ostia. In some embodiments, a combination of types and locations of electrodes can be used on balloon catheter ablation device 320. Energy can be delivered simultaneously or sequentially with the delivery of pharmacological agent, if so desired. In this fashion, delivery of ablation energy and antimitotic pharmacological agent droplets 232 can take place in a temporally coordinated manner from balloon catheter ablation device 320 to surrounding tissue.

Figure 3C:
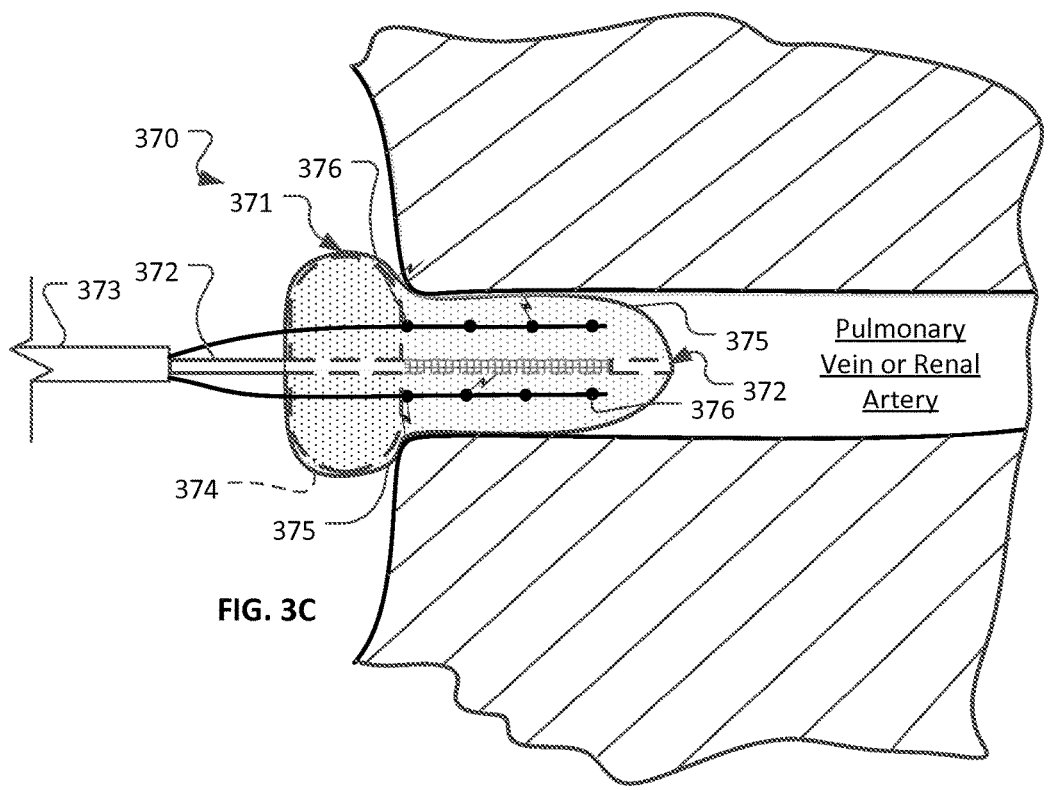
FIG. 3C is a schematic illustration of another balloon catheter that is capable of simultaneously delivering ablation energy and a stenosis prevention agent in accordance with some embodiments provided herein.

FIG. 3C illustrates another embodiment of a balloon catheter ablation device 370 with a bulbous proximal portion 371 and a generally cylindrical distal balloon portion 372. In this example implementation, balloon catheter ablation device 370 is depicted as making contact with tissue surrounding the ostium of a pulmonary vein or renal vein, and projecting into the pulmonary vein or renal vein.

In this embodiment, the bulbous proximal shape is achieved by having an internal balloon 374 (shown in dashed lines) inside of an outer balloon 375. Internal balloon 374 has an inflated diameter that is larger than the diameter of the inflated generally cylindrical distal portion of outer balloon 375. Each of the balloons 374 and 375 is supplied with inflation media via an individually discrete lumen. That is, central catheter 372 has a first lumen that is in fluid communication with the inner balloon 374 and a separate second lumen that is fluid communication with the outer balloon 375.

In some implementations of balloon catheter ablation device 370, inner balloon 374 is inflated with a gas such as air or carbon dioxide. Outer balloon 375, in contrast, can be inflated with a pharmacological agent that can, in some embodiments, be eluted through a porous or microporous material of outer balloon 375 to thereby make contact with the tissue of the pulmonary vein or renal artery to provide a therapeutic effect. For example in some embodiments the exudation and elution of a liquid pharmacological agent can serve to the prevent or reduce vessel stenosis and neointimal hyperplasia. For instance, the drug paclitaxel is an example of one type of an antimitotic pharmacological agent that can be delivered to the tissue undergoing ablation to prevent or reduce fibrosis and stenosis of the tissue. Paclitaxel can be used beneficially because of its rapid uptake and prolonged retention. In some implementations, paclitaxel can be delivered in 3% saline (or similar hypertonic solution) to further enhance its uptake and retention. While paclitaxel is provided as an example, other pharmacological agents can also be used.

In some embodiments, the pharmacological agent can transmit ablation energy as described in reference to, for example, balloon ablation device 200 of FIG. 2A. At the same time (if desired), or before or after delivery of the pharmacological agent, surface electrodes 376 can be activated to provide ablation energy to surrounding tissue. In this fashion, delivery of ablation energy and antimitotic pharmacological agent can take place in a coordinated fashion from balloon catheter ablation device 370 to surrounding tissue including the ostium of a pulmonary vein or renal vein, and projecting into the pulmonary vein or renal vein. Such methods may further comprise energizing one or more electrodes for enhancing an uptake of the pharmacological agent by the tissue.

Figure 3D:
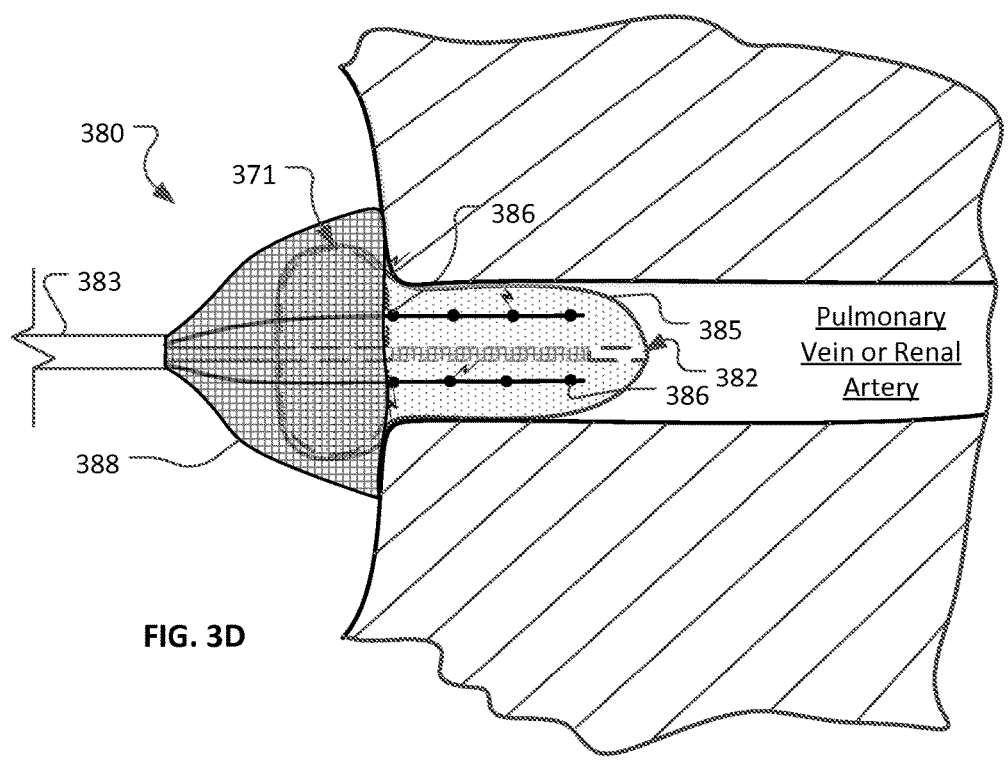
FIG. 3D is the schematic diagram of FIG. 3C showing the use of another embodiment of a balloon catheter that is capable of providing a coordinated delivery of ablation energy and a stenosis prevention agent.

With reference to FIG. 3D, another example embodiment of a balloon catheter ablation device 380 includes a bulbous proximal portion 381, a generally cylindrical distal balloon portion 382, and a filter device 388. In this example implementation, balloon catheter ablation device 380 is depicted as making contact with tissue surrounding the ostium of a pulmonary vein or renal vein, and projecting into the pulmonary vein or renal vein. Filter device 388 is configured to maintain full-wall apposition against the topography defined by the tissue surrounding the ostium of the pulmonary vein or renal vein.

Filter device 388 is configured to provide embolic protection. For example, filter device 388 can capture emboli such as blood clots, plaque, tissue fragments, shards or particles of pharmacological agents, and the like. In some circumstances, some such emboli may be generated or may become embolic as a result of the use of balloon catheter device 380.

Filter device 388 can be constructed, configured, and operated as described above in reference to filter device 186 (refer to FIG. 1C).

In some embodiments, filter device 388 can additionally or alternatively be configured to substantially occlude blood flow around the region of balloon catheter ablation device 380 and the pulmonary vein or renal artery. In some such embodiments, the pore size of filter device 388 can be selected so that filter device 388 will occlude all or substantially all blood flow therethrough. In this manner, blood flowing between balloons 381/382 and the tissue walls can be reduced or eliminated as desired. Similarly, blood flowing in the space between filter device 388 and vessel ostia can be reduced or eliminated as desired. By so controlling the blood flow using filter device 388, the therapeutic efficacy of balloon catheter ablation device 380 can be enhanced in some circumstances. For example, in some circumstances the uptake of liquid pharmacological agents and/or the transfer of ablation energy from balloon catheter device 380 to the surrounding tissue can be enhanced by controlling the blood flow using filter device 388.

Figure 4:
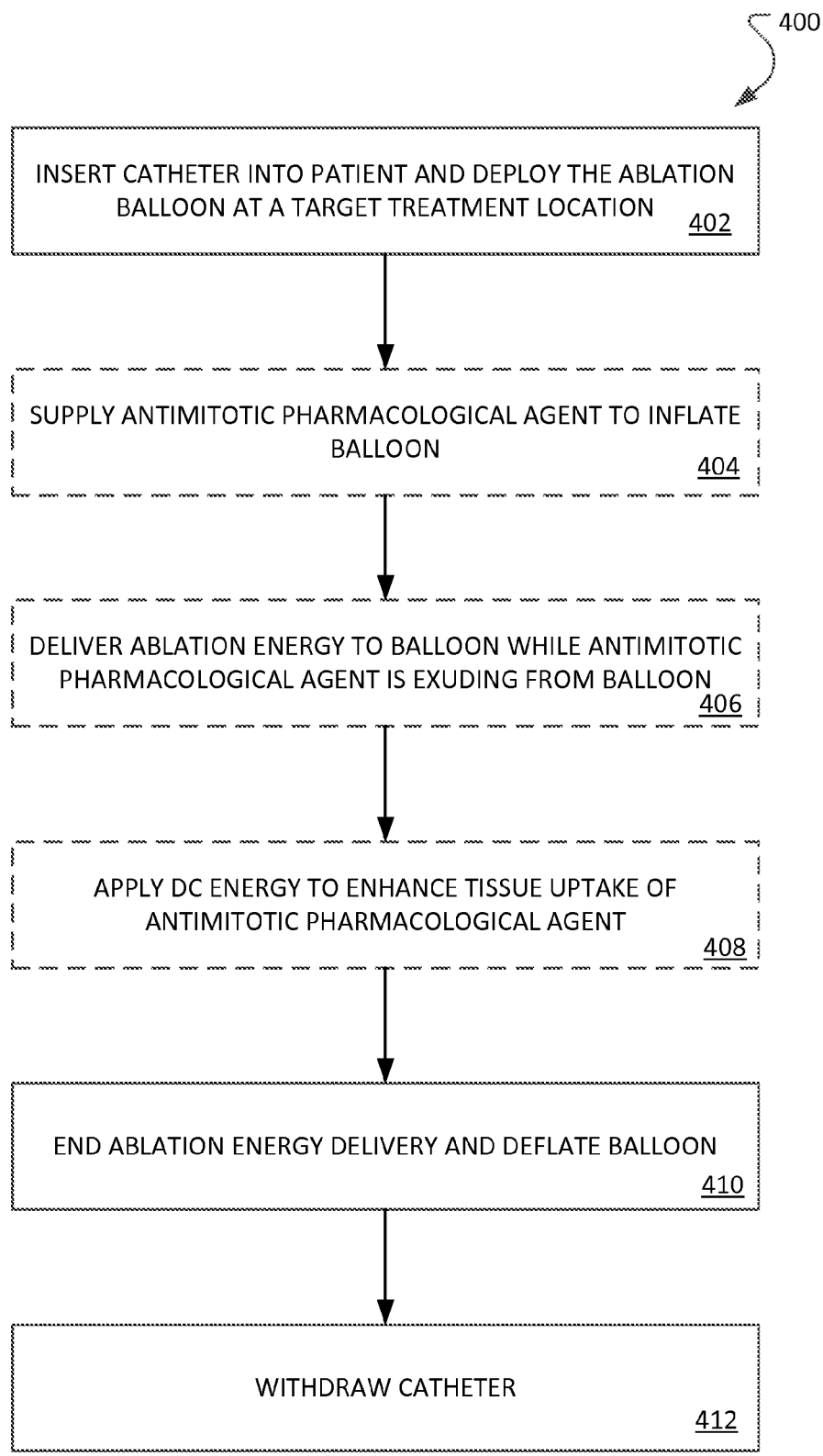
FIG. 4 is flowchart of an exemplary ablation method in accordance with some embodiments provided herein.

With reference to FIG. 4, a flowchart of a process 400 for ablating a target tissue while simultaneously delivering an antimitotic pharmacological agent to prevent or reduce stenosis of the tissue is provided. In general, process 400 uses a catheter-based balloon ablation device, such as those described herein, that is sized and shaped to be used with the particular patient anatomy to be ablated.

At operation 402, a catheter is inserted into a patient by a clinician. In some cases, a guidewire is inserted first and the catheter is inserted over or on the guidewire. The catheter can be a delivery catheter or sheath which contains a balloon catheter with a distally located balloon device in a deflated state. The balloon device can be porous or microporous such that a liquid can be made to exude, elute, or weep out from the balloon device as described herein. The balloon catheter can also include one or more electrodes for the delivery of energy to the patient's tissue. The delivery catheter and/or the balloon catheter can include one or more radiopaque markers to assist with radiographically visualizing the positioning of the catheters within the patient. The catheters can be routed within the patient to a position where the distal end of the delivery catheter is near the target treatment location (e.g., a pulmonary vein as described in reference to FIGS. 1 and 3A, or other treatment locations as desired). The clinician can cause the balloon device to emerge from the delivery catheter into a desired position at the target treatment site.

At operation 404, the clinician can optionally supply an antimitotic pharmacological agent solution through a lumen of the balloon catheter to infill the balloon device at the distal end of the balloon catheter. The delivery of the solution will cause the balloon device to inflate and make contact with surrounding tissue. Pressurizing the balloon device with the antimitotic pharmacological agent can also cause some of the antimitotic pharmacological agent to exude, elute, or weep from the balloon device to the surrounding tissue. The antimitotic pharmacological agent can prevent or reduce fibrosis and stenosis of the tissue. In other embodiments, as an alternative to using the antimitotic pharmacological agent solution to infill the balloon device, the balloon device can be drug-coated and a different type of inflation fluid can be used (e.g. saline). In still other embodiments, the balloon device can be drug-coated and an antimitotic pharmacological agent solution can be used to infill the balloon device. In still other embodiments, no pharmacological agent is administered directly from the balloon device.

At operation 406, the clinician can optionally cause ablation energy to be delivered to the one or more electrodes at the balloon device. This operation can optionally be temporally coordinated before, concurrently, and/or after the exuding of the antimitotic pharmacological agent in operation 404 as desired. The ablation energy can cause ablation or denervation of the tissue at the target treatment location. At the same time, the antimitotic pharmacological agent delivered to the tissue can prevent or reduce the occurrence of stenosis of the tissue receiving the ablation.

At operation 408, the clinician can optionally cause DC energy to be supplied to one or more electrodes on the balloon device. The provision of such energy can assist with the uptake of the antimitotic pharmacological agent into the tissue.

At operation 410, the ablation energy is discontinued and the balloon device is deflated. In some cases, the effects of the process operations above can be monitored and repeated as necessary, or the catheters can be repositioned to treat another target treatment location within the patient.

At operation 412, the catheters are withdrawn from the patient to conclude the treatment process 400.

Figure 5B:
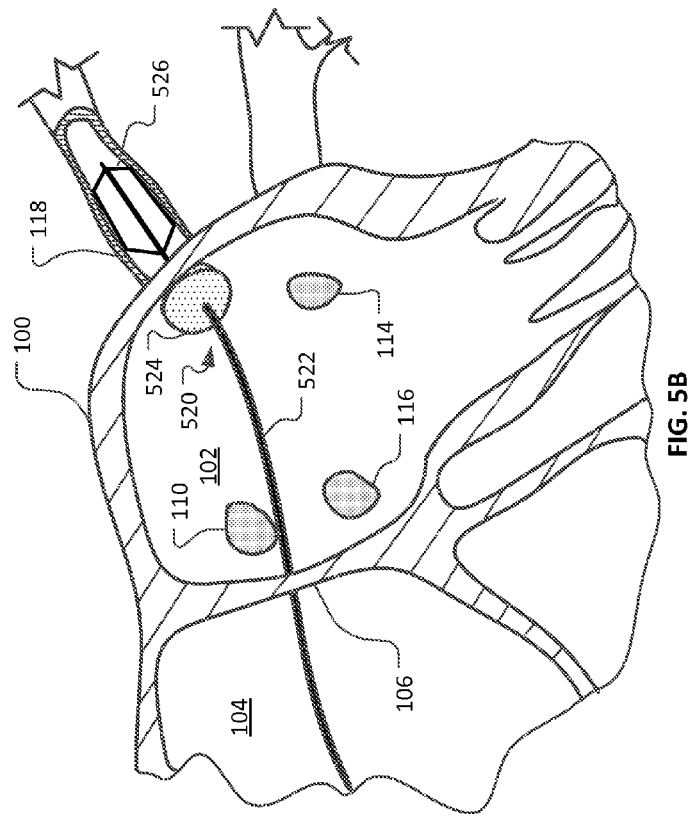
FIG. 5B is a schematic diagram of heart undergoing a pulmonary vein ablation using the catheter-based device of FIG. 5A in accordance with some embodiments provided herein.
Figure 5A:
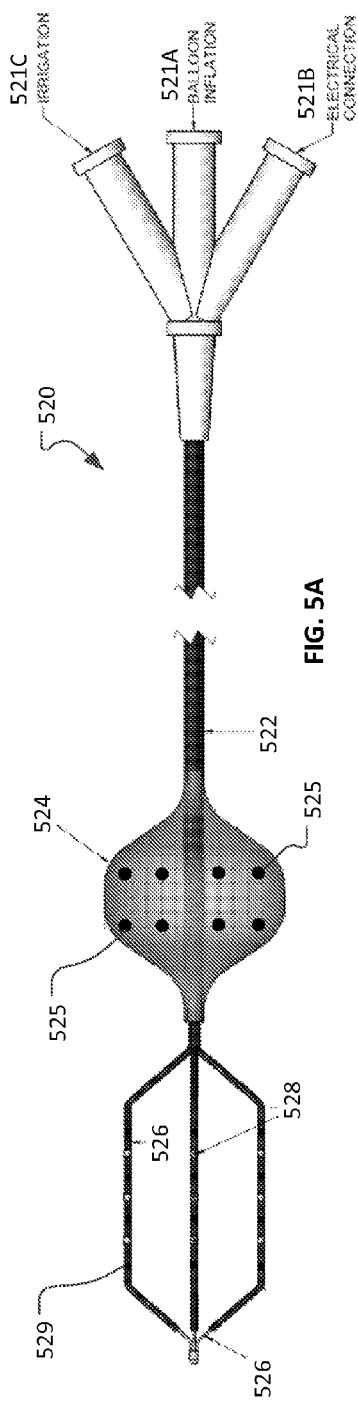
FIG. 5A is a schematic illustration of another ablation device that is capable of simultaneously delivering ablation energy and a stenosis prevention agent in accordance with some embodiments provided herein.

FIG. 5A is an illustration of another ablation device 520 that is capable of simultaneously delivering ablation energy and a stenosis prevention agent in accordance with some embodiments provided herein. Ablation device 520 includes a central catheter 522 that has multiple lumens. Mounted to central catheter 522 is a balloon device 524 (shown in an inflated configuration) and an expandable framework 526 (shown in an expanded configuration). In some implementations, balloon device 524 and expandable framework 526 are collapsed to low-profile configurations and placed within a delivery sheath (not shown) in preparation for delivery of ablation device 520 to a target location (e.g., a pulmonary vein or renal artery) within a patient.

One of the lumens of central catheter 522 is in fluid communication with balloon 524. As such, an inflation fluid can be supplied via a balloon inflation port 521A to inflate balloon 524. In some embodiments, the inflation fluid is a pharmacological agent that can exude, weep, or otherwise be transmitted through the balloon wall and to the tissue in contact with balloon 524. In some embodiments, balloon 524 is coated with a pharmacological agent. In still other embodiments, no pharmacological agent is administered by balloon 524.

In some embodiments, balloon 524 includes multiple electrodes 525 on the surface of balloon 524 that are supplied with electrical energy from one or more electrical connections 521B. Electrodes 525 can be configured for either monopolar or bipolar ablation techniques, or both can be used in some embodiments. Ablation energy sources such as RF, DC, AC in non-cardiac applications, cryogenics, hot solutions, and the like, and combinations thereof, can be used with ablation device 520. In some embodiments, both DC and RF electrodes 525 can be advantageously used in combination. That is, RF electrodes may be included because they are well-suited for delivering ablation energy, while DC electrodes may also be included because they are well-suited as iontophoretic sources for driving the pharmacological agents into tissue. The use of DC and RF electrodes 525 in combination can thereby provide a device that provides the benefits of both types of electrodes 525.

At the distal end portion of ablation device 520 is framework 526. Framework 526 can be made from a compliant material, and in some cases, a super-elastic material. For example, framework 526 can be made of a compliant polymeric material, a metallic material such as nitinol or stainless steel, or combinations of such materials. The super-elastic properties of nitinol make it a good choice for construction framework 526, however other materials can also be used. As mentioned previously, framework 526 can be elastically collapsed to a low-profile configuration for placement within a delivery sheath. Upon emergence from the delivery sheath at the target location within a patient, framework 526 can self-expand such that the individual tubular members of framework 526 make contact with the tissue of the patient (e.g., the wall of the pulmonary vein or renal artery).

In some embodiments, framework 526 includes multiple surface electrodes 529, that can be the same types of electrodes as electrodes 525 (e.g., RF, DC, both RF and DC, etc.), or can be different types of electrodes (e.g., while electrodes 525 are DC, electrodes 529 may be RF, as one example). In addition, in some embodiments at least portions of framework 526 are comprised of tubing, and the tubing includes one or more ports 528 through which a pharmacological agent can exude, weep, or otherwise be transmitted. Such pharmacological agents can be supplied to ablation device 520 at an irrigation connection 521C. The pharmacological agent can travel through a lumen in central catheter 522 to framework 526.

As previously mentioned, in some embodiments at least portions of framework 526 are elongate tubular members. In some embodiments, multiple tubular members are coupled together to form framework 526. For example, in some embodiments, three elongate tubular members comprise the framework. In other embodiments, four, five, six, or more than six tubular members comprise the framework. The tubular members can support electrodes 529, and can include one or more ports 528. In some embodiments, the tubular members, being hollow, convey a pharmacological agent from central catheter 522 to ports 528, whereat the pharmacological agent emerges from the tubular members and contacts the tissue (e.g., the wall of the pulmonary vein or renal artery).

In reference to FIG. 5B, heart 100 is depicted as receiving an ablation procedure using the example ablation device 520. Balloon device 524 is in contact with (or near), and delivers ablation energy to, the tissue surrounding the ostium of pulmonary vein 118. Framework 526 is located within pulmonary vein 118 and in an expanded configuration such that ablation energy can be delivered from electrodes 529 (refer to FIG. 5A) to the inner wall of pulmonary vein 118. In addition, in some embodiments one or more pharmacological agents can be administered by ablation device 520. For example, a pharmacological agent(s) can be administered via ports 528 in framework 526 and/or via balloon 524. However, in some embodiments no such pharmacological agents are administered.

Figure 6B:
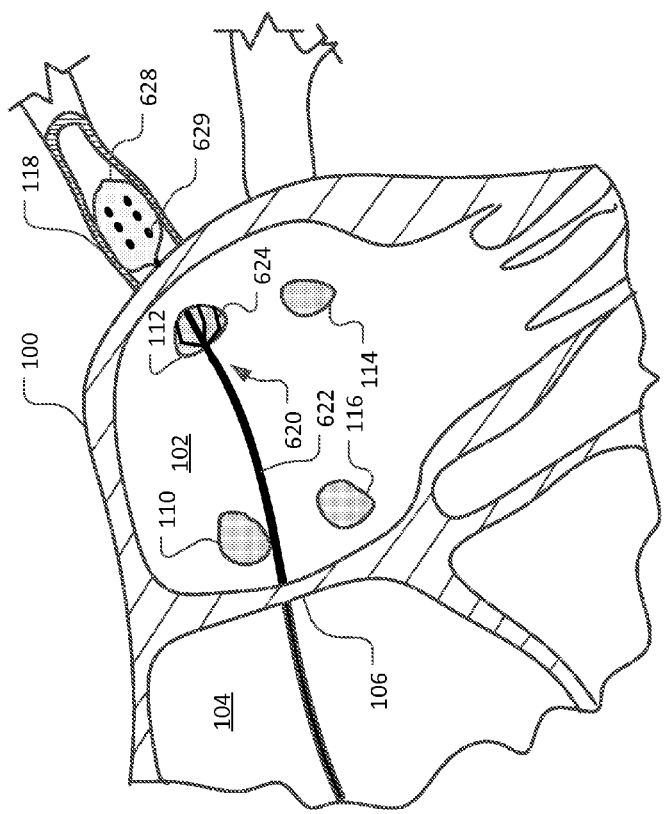
FIG. 6B is a schematic diagram of heart undergoing a pulmonary vein ablation using the catheter-based device of FIG. 6A in accordance with some embodiments provided herein.
Figure 6A:
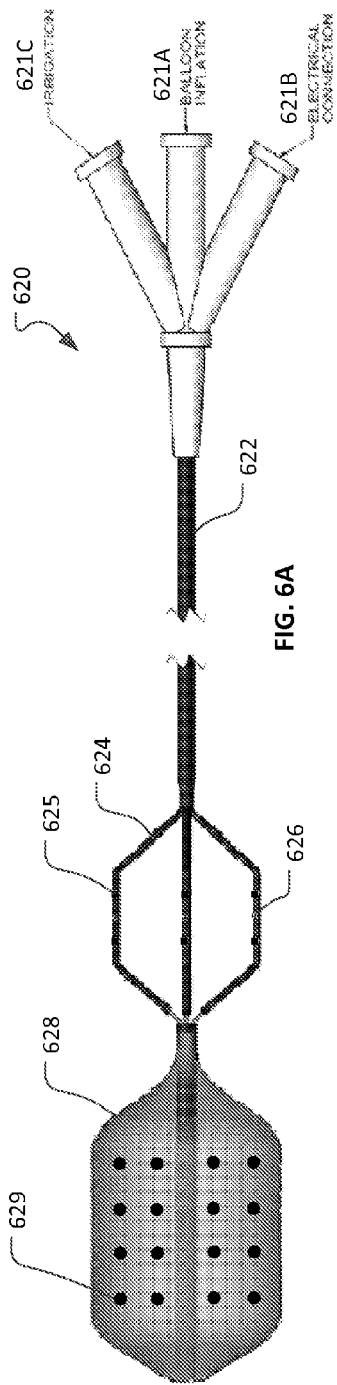
FIG. 6A is a schematic illustration of another ablation device that is capable of simultaneously delivering ablation energy and a stenosis prevention agent in accordance with some embodiments provided herein.

FIG. 6A is an illustration of another ablation device 620 that is capable of simultaneously delivering ablation energy and a stenosis prevention agent in accordance with some embodiments provided herein. Ablation device 620 includes a central catheter 622 that has multiple lumens. Mounted to central catheter 622 is a framework 624 (shown in an expanded configuration) and balloon device 628 (shown in an inflated configuration). In some implementations, framework 624 and balloon device 628 are collapsed to low-profile configurations and placed within a delivery sheath (not shown) in preparation for delivery of ablation device 620 to a target location (e.g., a pulmonary vein or renal artery) within a patient.

Framework 624 is made from a compliant material, or in some cases, a super-elastic material (such as described above in reference to framework 526). The super-elastic properties of nitinol make it a good choice for construction framework 624, however other materials can also be used. Framework 624 can be elastically collapsed to a low-profile configuration for placement within a delivery sheath. Upon emergence from the delivery sheath at the target location within a patient, framework 624 can self-expand such that the individual tubular members of framework 624 make contact with the tissue of the patient (e.g., the wall tissue of the pulmonary vein or renal artery, such as the tissue near to the ostium of pulmonary vein or renal artery).

In some embodiments at least portions of framework 624 are elongate tubular members. In some embodiments, multiple elongate tubular members are coupled together to form framework 624. For example, in some embodiments, three elongate tubular members comprise the framework. In other embodiments, four, five, six, or more than six elongate tubular members comprise the framework.

In some embodiments, framework 624 includes multiple surface electrodes 625, that can be the same types of electrodes and combinations of electrodes as described in reference to other ablation device embodiments provided herein. In addition, in some embodiments at least portions of framework 624 are comprised of tubing, and the tubing includes one or more ports 626 through which a pharmacological agent can exude, weep, or otherwise be transmitted. Such pharmacological agents can be supplied to ablation device 620 at an irrigation connection 621C. The pharmacological agent can travel through a lumen in central catheter 622 to framework 626. In some embodiments, the tubular members, being hollow, convey the pharmacological agent from central catheter 622 to ports 626, whereat the pharmacological agent emerges from the tubular members and contacts the tissue (e.g., the wall of the pulmonary vein or renal artery).

At the distal end portion of ablation device 620 is balloon device 628. A lumen of central catheter 622 is in fluid communication with balloon device 628. As such, an inflation fluid such as a pharmacological agent can be supplied via a balloon inflation port 621A to inflate balloon 628. In some embodiments, the inflation fluid is a pharmacological agent that can exude, weep, or otherwise be transmitted through the balloon wall and to the tissue in contact with balloon 628. In some embodiments, balloon 628 is coated with a pharmacological agent. In still other embodiments, no pharmacological agent is administered by balloon 628. In some embodiments, balloon 628 includes multiple electrodes 629 on the surface of balloon 628 that are supplied with electrical energy from one or more electrical connections 621B. Electrodes 629 can be configured for either monopolar or bipolar ablation techniques, or both can be used in some embodiments. Ablation energy sources such as RF, DC, AC in non-cardiac applications, cryogenics, hot solutions, and the like, and combinations thereof, can be used with ablation device 620. In some embodiments, both DC and RF electrodes 629 can be advantageously used in combination. That is, RF electrodes may be included because they are well-suited for delivering ablation energy, while DC electrodes may also be included because they are well-suited as iontophoretic sources for driving the pharmacological agents into tissue. The use of DC and RF electrodes 629 in combination can thereby provide a device that provides the benefits of both types of electrodes 629.

In reference to FIG. 6B, heart 100 is depicted as receiving an ablation procedure using the example ablation device 620. Framework 624 is in an expanded configuration and in contact with (or near) the tissue near the ostium of pulmonary vein 118. Balloon 628 is located within pulmonary vein 118 and in an inflated configuration such that ablation energy can be delivered from electrodes 629 to the inner wall of pulmonary vein 118. In addition, in some embodiments one or more pharmacological agents can be administered by ablation device 620. For example, a pharmacological agent(s) can be administered via ports 626 in framework 624 and/or via balloon 628. However, in some embodiments no such pharmacological agents are administered directly from the ablation device.

Figure 7A:
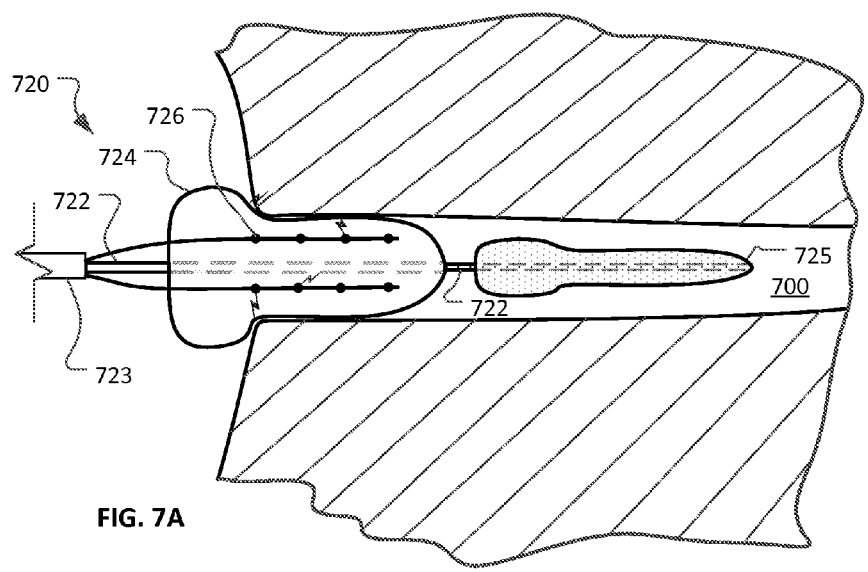
FIGS. 7A and 7B are illustrations of a balloon catheter ablation device with a first balloon that can deliver ablation energy and a second balloon that can deliver a stenosis prevention agent in accordance with some embodiments provided herein.
Figure 7B:
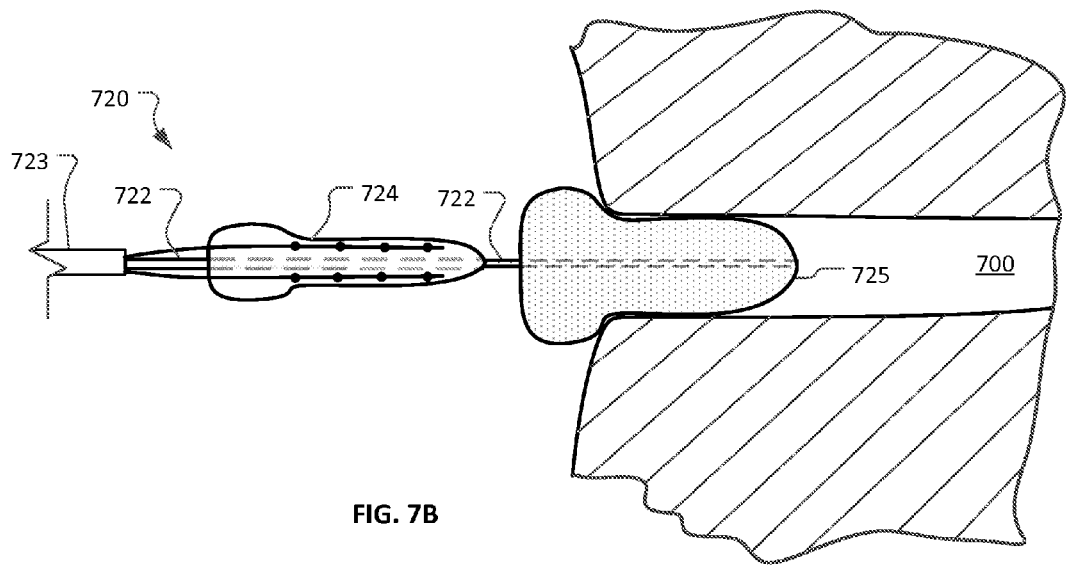

FIGS. 7A and 7B illustrate the use of a balloon catheter ablation device 720 that includes a first balloon 724 that can deliver ablation energy and a second balloon 725 that can deliver a stenosis prevention agent. FIG. 7A illustrates a medical procedural step during which ablation energy is applied to tissue from electrodes 726 of first balloon 724. FIG. 7B illustrates a step during which an antimitotic pharmacological agent can administered to the tissue from second balloon 725. While these two steps are sequential operations, they can be performed in either order.

In the depicted embodiment, both balloons 724 and 725 of balloon catheter ablation device 720 have bulbous proximal portions. In alternative embodiments, one or both of balloons 724 and 725 may other shapes. For example, first balloon 724 may have a bulbous proximal portion, but second balloon 725 may be generally cylindrical. Or, first balloon 724 may be generally cylindrical and second balloon 725 may have a bulbous proximal portion. Or, in other embodiments, both balloons 724 and 725 may be generally cylindrical. Other shapes may also be used.

In some embodiments, both balloons 724 and 725 are coupled to catheter shaft 722. However, in alternative embodiments, multiple catheters may be used so that the balloons 724 and 725 can be moved independently of each other. In some embodiments, balloons 724 and 725 are in fluid communication with lumens of catheter 722 that are independent of each other. That is, in such embodiments, first balloon 724 is in fluid communication with a first lumen of catheter 722, while second balloon 725 is in fluid communication with a second lumen of catheter 722 (and the first and second lumens are discreetly separate from each other). However, in alternative embodiments, a single lumen of catheter 722 is in fluid communication with both balloons 724 and 725.

It should be understood that any of the ablation energy delivery modalities described herein can be utilized in regard to first balloon 724. Further, any of the modalities described herein for the delivery of an antimitotic pharmacological agent can be utilized in regard to the second balloon 725.

Figure 8A:
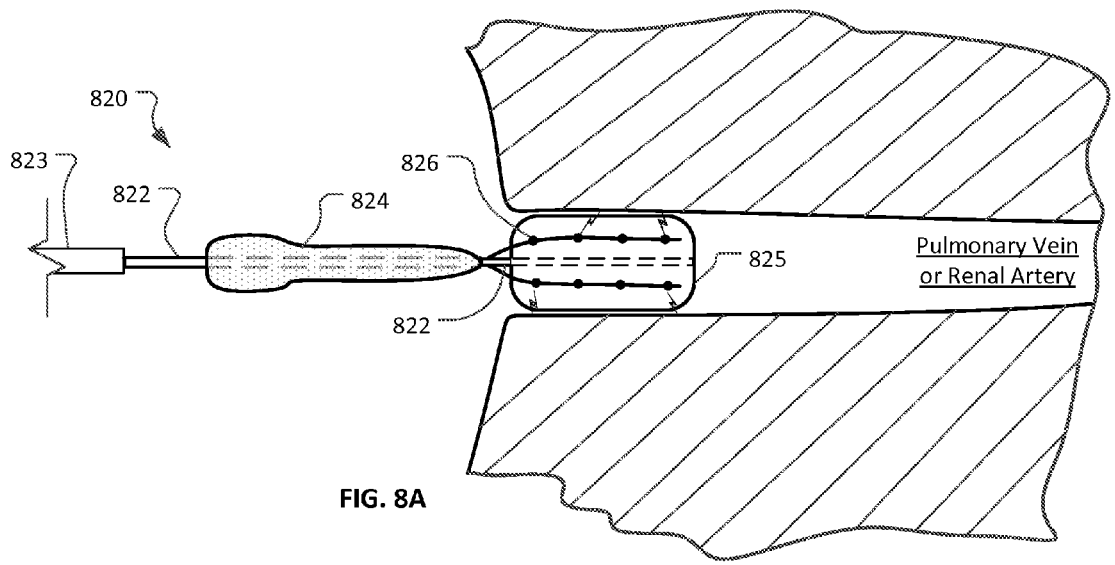
FIGS. 8A and 8B are illustrations of another balloon catheter ablation device with a first balloon that can deliver ablation energy and a second balloon that can deliver a stenosis prevention agent in accordance with some embodiments provided herein.
Figure 8B:
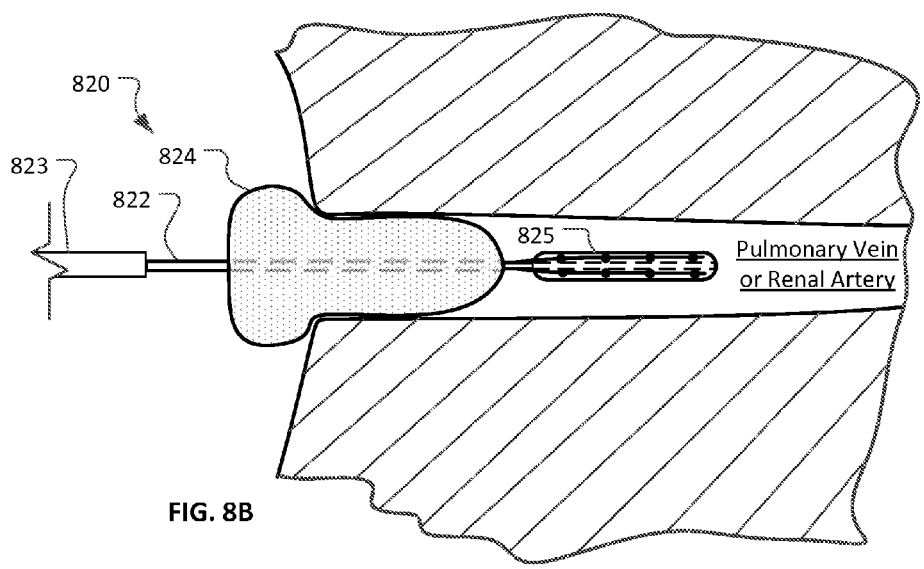

FIGS. 8A and 8B illustrate the use of a balloon catheter ablation device 820 that includes a first balloon 824 that can deliver a stenosis prevention agent and a second balloon 825 that can deliver ablation energy. FIG. 8A illustrates a step during which ablation energy is applied to tissue from electrodes 826 of second balloon 825. FIG. 8B illustrates a step during which an antimitotic pharmacological agent can administered to the tissue from first balloon 824. While these two steps are sequential operations, they can be performed in either order.

In the depicted embodiment, first balloon 824 has a bulbous proximal portion, while second balloon 825 is generally cylindrical. In alternative embodiments, first balloon 824 may be generally cylindrical, while second balloon 825 has a bulbous proximal portion. In still other embodiments, both balloons 824 and 825 may have bulbous proximal portions, or both may be generally cylindrical. Other shapes of balloons, in addition to generally cylindrical and proximally bulbous, may also be used.

In some embodiments, both balloons 824 and 825 are coupled to catheter shaft 822. However, in alternative embodiments, multiple catheters may be used so that the balloons 824 and 825 can be moved independently of each other. In some embodiments, balloons 824 and 825 are in fluid communication with lumens of catheter 822 that are independent of each other. That is, in such embodiments, first balloon 824 is in fluid communication with a first lumen of catheter 822, while second balloon 825 is in fluid communication with a second lumen of catheter 822 (and the first and second lumens are discreetly separate from each other). However, in alternative embodiments, a single lumen of catheter 822 is in fluid communication with both balloons 824 and 825.

It should be understood that any of the ablation energy delivery modalities described herein can be utilized in regard to second balloon 825. Further, any of the modalities described herein for the delivery of an antimitotic pharmacological agent can be utilized in regard to the first balloon 824.

It should also be understood, that the features and usage techniques described herein in relation to the various ablation devices can be combined with the features of other ablation device embodiments and usage techniques described herein. Accordingly, based on such combinations and sub-combinations, an extensive number of ablation device embodiments and usage techniques are envisioned and provided herein.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A catheter-based medical device for treating a tissue, the device comprising:
   an elongate catheter shaft including a liquid delivery lumen therethrough;
   a balloon device disposed at a distal end portion of said catheter shaft, said balloon device comprising a bulbous-shaped proximal portion and a generally cylindrical-shaped distal portion when said balloon is inflated, said bulbous-shaped proximal portion in fluid communication with said generally cylindrical-shaped distal portion, said balloon device comprising an outer surface and an inner surface, said inner surface defining an interior space of said balloon device, said balloon device in fluid communication with said liquid delivery lumen, said balloon device comprising a porous or microporous material that is arranged to transmit a liquid through said porous or microporous material;

one or more electrodes that are disposed on or within said balloon device and are arranged to deliver energy to said tissue; and a filter device that is reconfigurable between a collapsed low-profile delivery configuration and a deployed configuration in which said filter device is radially expanded in comparison to said collapsed low-profile delivery configuration, wherein said bulbous-shaped proximal portion of said balloon device is inside said filter device while said filter device is configured in said deployed configuration.

2. The catheter-based medical device of claim 1, wherein said one or more electrodes is a single electrode disposed on said catheter shaft and in said interior space.

3. The catheter-based medical device of claim 2, wherein said single electrode is arranged to transmit radio frequency energy for ablation of said tissue.

4. The catheter-based medical device of claim 1, wherein said one or more electrodes is a plurality of electrodes disposed on said outer surface.

5. The catheter-based medical device of claim 4, wherein said plurality of electrodes comprise at least one electrode that is arranged to transmit radio frequency energy for ablation of said tissue and at least one electrode that is arranged to transmit direct current electrical energy.

6. The catheter-based medical device of claim 1, wherein said one or more electrodes comprises (i) a single electrode disposed on said catheter shaft and in said interior space and (ii) plurality of electrodes disposed on said outer surface.

7. The catheter-based medical device of claim 6, wherein said single electrode is arranged to transmit radio frequency energy for ablation of said tissue, and said plurality of electrodes comprise at least one electrode that is arranged to transmit direct current electrical energy.

8. The catheter-based medical device of claim 1, wherein said filter device comprises a material that captures emboli while allowing transmission of blood flow therethrough.

9. The catheter-based medical device of claim 1, wherein said filter device is configured to substantially prevent blood from flowing therethrough.

10. The catheter-based medical device of claim 1, wherein said filter device is biased to self-expand from said collapsed low-profile delivery configuration to said deployed configuration.

11. A catheter-based medical device for treating a tissue, the device comprising:
an elongate catheter shaft including a liquid delivery lumen therethrough;

a balloon device disposed at a distal end portion of said catheter shaft, said balloon device comprising a bulbous-shaped proximal portion and a generally cylindrical-shaped distal portion when said balloon is inflated, said bulbous-shaped proximal portion in fluid communication with said generally cylindrical-shaped distal portion, said balloon device comprising an outer surface and an inner surface, said inner surface defining an interior space of said balloon device, said balloon device in fluid communication with said liquid delivery lumen, said balloon device comprising a porous or microporous material that is arranged to transmit a liquid through said porous or microporous material;

one or more electrodes that are disposed on or within said balloon device and are arranged to deliver energy to said tissue; and a filter device, said filter device being deployable from said catheter shaft and generally coaxial with said balloon device, wherein said bulbous-shaped proximal portion of said balloon device is inside said filter device while said filter device is deployed, and wherein a distal end portion of said filter device is configured to contact a tissue surface surrounding said tissue.

12. The catheter-based medical device of claim 11, wherein said balloon device is configured to extend distally of said filter device when said filter device and said balloon device are extended from said catheter shaft in a configuration to treat said tissue.

13. The catheter-based medical device of claim 11, wherein said filter device is configured to substantially prevent blood from flowing therethrough.

14. The catheter-based medical device of claim 11, wherein said filter device comprises a material that captures emboli while allowing transmission of blood flow therethrough.

* * * * *

UNITED STATES PATENT AND TRADEMARK OFFICE
CERTIFICATE OF CORRECTION

PATENT NO. : 10,390,879 B2
APPLICATION NO. : 14/892035
DATED : August 27, 2019
INVENTOR(S) : Samuel J. Asirvatham and David R. Holmes, Jr.

Page 1 of 1

It is certified that error appears in the above-identified patent and that said Letters Patent is hereby corrected as shown below:

In the Specification

Column 1, Lines 9-10, delete "May 22, 2014," and insert -- May 20, 2014, --.

Signed and Sealed this
Seventh Day of July, 2020

Andrei Iancu
*Director of the United States Patent and Trademark Office*